(12) United States Patent
Feferberg

(10) Patent No.: US 11,433,259 B2
(45) Date of Patent: Sep. 6, 2022

(54) INTERNAL ORGAN, INJURY AND PAIN TREATMENT

(71) Applicant: B.R.H. Medical Ltd., Jerusalem (IL)

(72) Inventor: Ilan Feferberg, Rishon LeZion (IL)

(73) Assignee: B.R.H. Medical Ltd., Jerusalem (IL)

( * ) Notice: Subject to any disclaimer, the term of this patent is extended or adjusted under 35 U.S.C. 154(b) by 285 days.

(21) Appl. No.: 16/628,769

(22) PCT Filed: Jul. 4, 2018

(86) PCT No.: PCT/IL2018/050727
§ 371 (c)(1),
(2) Date: Jan. 6, 2020

(87) PCT Pub. No.: WO2019/008582
PCT Pub. Date: Jan. 10, 2019

(65) Prior Publication Data
US 2020/0139160 A1  May 7, 2020

Related U.S. Application Data

(60) Provisional application No. 62/657,944, filed on Apr. 16, 2018.

(30) Foreign Application Priority Data

Jul. 4, 2017 (IL) .......................................... 253301

(51) Int. Cl.
*A61N 7/00* (2006.01)
*A61N 1/06* (2006.01)

(52) U.S. Cl.
CPC ................ *A61N 7/00* (2013.01); *A61N 1/06* (2013.01); *A61N 2007/0017* (2013.01); *A61N 2007/0052* (2013.01); *A61N 2007/0073* (2013.01)

(58) Field of Classification Search
CPC .... A61N 7/00; A61N 1/06; A61N 2007/0017; A61N 2007/0052; A61N 2007/0073;
(Continued)

(56) References Cited

U.S. PATENT DOCUMENTS 5,859,527 A    1/1999  Cook
6,217,530 B1   4/2001  Martin et al.
(Continued)

FOREIGN PATENT DOCUMENTS

CN    104582606 A    4/2015
RU      2428223 C2   9/2011
(Continued)

OTHER PUBLICATIONS

Johnsen, Gorm K.,"Skin electrical properties and physical aspects of hydration of keratinized tissues", Thesis submitted for the degree of Philosophiae Doctor, Department of Physics, University of Oslo, Jun. 2010.
(Continued)

*Primary Examiner* — Hien N Nguyen
(74) *Attorney, Agent, or Firm* — Elmore Patent Law Group, P.C.; Carolyn Elmore; Joseph Zucchero

(57) ABSTRACT

Ultrasound (US) apparatus and method for applying low energy US onto an internal tissue/organ, including a non-invasive US appliance used on a treatment region over the internal tissue/organ, and an electrical stimulation apparatus for simultaneously inducing interferential electrical stimulation. A controller controls parameters of the electrical stimulation apparatus and the US appliance, and dynamically changes at least one of the parameters, for maintaining the impedance of the body tissue in the treatment region within an impedance range. The US apparatus includes an impedance monitoring apparatus for continuously measuring, tracking, and monitoring impedance in the treatment
(Continued)

region, wherein the controller dynamically changes at least one of the parameter in response to the impedance as monitored, for maintaining the impedance within the predefined range. The internal tissue/organ can be a female fertility organ, which can be, an ovarian follicle, a blood vessel of the uterus (womb), the ovary, the endometrial lining, and the Fallopian tube, ulcer, closed wound, internal injury, inflammation. and nerves.

20 Claims, 7 Drawing Sheets

(58) Field of Classification Search
CPC .. A61N 1/323; A61N 1/36014; A61N 1/0468; A61N 1/0456; A61N 2007/0021; A61N 2007/0026; A61N 1/36021; A61N 1/36031; A61N 2007/0047; A61B 2018/00559; A61B 2018/00791; A61B 2018/00875; A61B 2090/378; A61B 5/053; A61B 8/08
See application file for complete search history.

(56) References Cited

U.S. PATENT DOCUMENTS

| | | | |
|---|---|---|---|
| 6,470,216 | B1 | 10/2002 | Knowlton |
| 6,745,078 | B1 | 6/2004 | Buchner |
| 7,494,488 | B2 | 2/2009 | Weber |
| 7,510,536 | B2 | 3/2009 | Foley et al. |
| 7,520,856 | B2 | 4/2009 | Vaezy et al. |
| 7,623,924 | B2 | 11/2009 | Narciso, Jr. |
| 7,727,152 | B2 | 6/2010 | Qin et al. |
| 7,914,469 | B2 | 3/2011 | Torbati |
| 8,079,966 | B2 | 12/2011 | El-bialy et al. |
| 8,292,834 | B2 | 10/2012 | El-bialy et al. |
| 8,337,434 | B2 | 12/2012 | Vaezy et al. |
| 8,465,427 | B1 | 6/2013 | Qin |
| 2007/0038098 | A1 | 2/2007 | Harris |
| 2007/0255267 | A1 | 11/2007 | Diederich et al. |
| 2009/0171138 | A1 | 7/2009 | Eli |
| 2010/0228126 | A1 | 9/2010 | Emery et al. |
| 2013/0267975 | A1* | 10/2013 | Timm .................... H01H 23/28 606/169 |
| 2013/0289416 | A1 | 10/2013 | Feferberg |
| 2015/0148712 | A1 | 5/2015 | Loven et al. |
| 2017/0050019 | A1 | 2/2017 | Ron Edoute et al. |
| 2017/0128722 | A1 | 5/2017 | Perez |
| 2018/0028841 | A1 | 2/2018 | Konofagou et al. |
| 2019/0028841 | A1 | 1/2019 | Schlesinger et al. |

FOREIGN PATENT DOCUMENTS

| | | |
|---|---|---|
| WO | 2012085920 A1 | 6/2012 |
| WO | 2014004116 A1 | 1/2014 |

OTHER PUBLICATIONS

Search Report dated Jul. 6, 2021 in IL Application No. 277084.
Baker, L. L. et al., "Effects of electrical stimulation on wound healing in patients with diabetic ulcers", Diabetes Care, 20(3), DOI: 10.2337/diacare.20.3.405, Mar. 1997, 405-412.
Dyson, M. et al., "Stimulation of healing of varicose ulcers by ultrasound", Ultrasonics, 14(5), DOI: 10.1016/0041-624x(76)90024-x, Sep. 1976, 232-236.
Vaezy, S. et al., "Use of high-intensity focused ultrasound to control bleeding", J. Vasc. Surg., 29(3), DOI:https://doi.org/10.1016/S0741-5214(99)70282-X, Mar. 1, 1999, 533-542.

* cited by examiner

INTERNAL ORGAN, INJURY AND PAIN TREATMENT

RELATED APPLICATIONS

This application U.S. National stage entry of International Application No. PCT/IL2018/050727, which designated the United States and was filed on Jul. 4, 2018, published in English which claims priority to Israel Application No. 253301, filed Jul. 4, 2017 which claims the benefit of U.S. Provisional Application No. 62/657,944, filed Apr. 16, 2018. The entire teachings of the above applications are incorporated herein by reference.

FIELD OF THE DISCLOSED TECHNIQUE

The disclosed technique relates to systems and methods for applying ultrasound (US) energy in vivo treatment of internal tissue and organs of the human and mammal body, and in particular concerns treating an internal closed wound, ulcer, injury or inflammation, particularly of diabetic background, and enhancing female fertility.

BACKGROUND OF THE DISCLOSED TECHNIQUE

Non-invasive ultrasound (US) treatment of internal organs within the body of a patient, which are covered by thick layers of body tissue is difficult to treat in comparison with US treatment of superficial organs and tissue (e.g., skin, subcutaneous fat), since US energy must be conveyed directly from the external US generating apparatus to the internal organ through all the tissue layers disposed in between and separating the internal organ from the US generating head. The US energy quickly dissipates through the separating tissue layers, and pre-calculation and measuring of the correct intensity of US energy which is required to reach the internal organ for its effective treatment is very complicated, even with a focus US head. As a side effect, the separating tissues that absorb the major portion of the US energy may be severely damaged in the process. Female fertility organs are delicate internal organs that are typically surrounded by massive tissue layers that frustrate effective non-invasive US treatment thereof, without endangering the massive separating layers. This is also the case of treating any internal tissue, such of a closed wound, internal injury, inflammation and an internal ulcer. Diabetes often involves closed internal wounds and ulcers, typically in peripheral organs, often accompanied with damage to nerve cells, which may be developing in correlation to the progression of diabetic ulcer.

US Patent Application Publication No. 2013/289416 A1 (of the present inventor) discloses a system and method for treating skin ulcer, such as diabetic ulcer, on a treatment region of the body. Interferential electric stimulation is simultaneously applied with ultrasound energy. Operating parameters of the interferential electric stimulation, may be changed, in an arbitrary manner or according to a predetermined pattern, to prevent the body from adapting to the applied electrical stimulation.

U.S. Patent Application Publication No. 2007/0255267, to Diederich et al., entitled "Method of Thermal Treatment of Myolysis and Destruction of Benign Uterine Tumors", discloses a high-power ultrasound heating applicator for minimally-invasive thermal treatment of uterine fibroids or myomas. High-intensity interstitial ultrasound, is applied with minimally-invasive laparoscopic or hysteroscopic procedures, and is used to effectively treat fibroids within the myometrium in lieu of major surgery. The applicators are configured with high-power capabilities and thermal penetration to treat large volumes of fibroid tissue in short treatment times (3-20 minutes), while maintaining three-dimensional control of energy delivery to thermally destroy the target volume.

U.S. Patent Application Publication No. 2009/0171138, to Eli, entitled "Ultrasonic Device for Fertility Control and Management and Navigation", discloses a device for fertility control and management through the application of acoustic energy, including ultrasound. Fertility management and control is applied for reducing or enhancing fertility and/or otherwise controlling one or more aspects of fertility and conception, including improving the ability to conceive.

SUMMARY OF THE DISCLOSED TECHNIQUE

In accordance with one aspect of the disclosed technique, there is thus provided a method for applying low energy ultrasound (US) energy from a non-invasive external US source to an internal body tissue/organ, the method including the procedures of:
  (a) determining a treatment region over the internal tissue/organ;
  (b) positioning onto the skin at the treatment region in proximity to the internal tissue/organ, two pairs of electrodes at crossed configuration of an electrical stimulation apparatus operational for inducing interferential electrical stimulation;
  (c) applying interferential electrical stimulation through the electrodes to the treatment region, by applying a first current at a first electric frequency and a first electric intensity via one of the two pairs of electrodes, and a second current at a second electric frequency and a second electric intensity via another of the pairs of electrodes, thereby defining an interference pattern of resonant waves that revolve at an interferential frequency in the treatment region;
  (d) transmitting ultrasound (US) waves at an US frequency and an US intensity to the treatment region simultaneously with the applying of interferential electrical stimulation;
  (e) continuously monitoring impedance tracked in the treatment region; and
  (f) dynamically changing at least one parameter of the electrical stimulation and the ultrasound, in response to the impedance as monitored, for maintaining the impedance of the body tissue in the treatment region within a predefined impedance range, wherein the parameter includes one of: (i) the interferential frequency; (ii) the interference pattern; (iii) the US frequency; and (iv) the US intensity.

Procedure (e) of continuously monitoring impedance may feature monitoring electrical impedance, monitoring mechanical impedance, monitoring body temperature, monitoring impedance between electrodes of electrical stimulation, monitoring impedance between particular transducers/sensors, monitoring impedance between said electrodes and particular transducers/sensors, monitoring impedance by US diagnostics, monitoring impedance by an imaging apparatus, and monitoring impedance by any combination of the above The procedure of dynamically changing may include:
  (a) when the impedance is monitored above the impedance range, at least one of:
    (1) reducing impedance by at least one of:

(i) increasing at least one of: the first electric intensity and the second electric intensity; and
(ii) reducing the interferential frequency by increasing frequency gap between the first electric frequency and the second electric frequency; and
(2) increasing US penetration depth by at least one of:
(i) decreasing US frequency; and
(ii) increasing US intensity; and
(b) when the electric impedance is monitored below the impedance range, at least one of:
(1) increasing impedance by at least one of:
(i) reducing at least one of: the first electric intensity and the second electric intensity; and
(ii) increasing the interferential frequency by reducing frequency gap between the first electric frequency and the second electric frequency; and
(2) decreasing US penetration depth by at least one of:
(i) increasing US frequency; and
(ii) decreasing US intensity.

The method may further include the procedure of:
(g) dynamically changing another of the at least one parameter at a second pace, which is slower than a first pace at which said at least one parameter is changed, wherein the intensity and frequency of the ultrasound waves are maintained within the ultrasound range, such that at least one pattern of resonant ultrasound waves is effected to momentarily reach the internal tissue/organ.

The procedure of determining the region to be treated over the internal tissue/organ may include using US diagnostics/imaging for the determining. The diagnostics/imaging may be combined with ultrasound (US) treatment apparatus.

The procedure of applying interferential electrical stimulation, may include applying electrical stimulation at intensity in the electrical stimulation range of 1-70 mA. The procedure of transmitting ultrasound waves may include transmitting ultrasound waves at intensity in the ultrasound range of 0.7 MHz-3.5 MHz, 0-2.1 Watt/cm$^2$.

The method may further include the procedure of massaging the treatment region simultaneously with the procedures of applying interferential electrical stimulation and transmitting ultrasound waves, the procedure of applying a gel onto skin at the treatment region before the procedure of transmitting ultrasound waves, or the procedure of repeating the method several times in one session.

The internal tissue/organ may be a female fertility organ, such as the ovarian follicle, blood vessel of the uterus (womb), the ovary, the endometrial lining, or the Fallopian tube, ulcer, inflammation, closed wound, internal injury, and nerves. The method may be directed at effectuating/reinvigorating intensifying menstrual bleeding, regulating irregular menstruation, restoring menstruation, thickening endometrial lining, increase blood flow to/in the vicinity of the female organ/internal tissue, increase ovary dimension, increase ovarian follicle dimension, altering hormones regime, clearing accretions, increasing hormone concentration, and treating ulcer, closed wound, internal injury, inflammation, and/or nerves.

In accordance with another aspect of the present technique there is provided an ultrasound (US) apparatus for applying low energy US onto an internal tissue/organ. The US apparatus includes a non-invasive external US appliance operational for applying low energy US energy, at an US frequency and an US intensity, onto a treatment region over the internal tissue/organ.

The US apparatus further includes an electrical stimulation apparatus including two pairs of electrodes operational for inducing interferential electrical stimulation configured for positioning at crossed configuration onto the skin at the treatment region in proximity to the internal tissue/organ, by applying, simultaneously with the applying US energy, a first current at a first electric frequency and a first electric intensity via one of the two pairs of electrodes, and a second current at a second electric frequency and a second electric intensity via another of the pairs of electrodes, thereby defining an interference pattern of resonant waves that revolve at an interferential frequency in the treatment region.

The US apparatus further includes an impedance monitoring apparatus for continuously tracking and monitoring the impedance of the body tissue in the treatment region.

The US apparatus further includes a controller for controlling parameters of the electrical stimulation apparatus and the US appliance, operational for dynamically changing at least one of the parameters, in response to the impedance monitored by said monitoring apparatus, for maintaining the impedance within a predefined impedance range, wherein the parameters are selected from the group of electrical stimulation parameters and ultrasound parameters consisting of: (i) the interferential frequency; (ii) the interference pattern; (iii) the US frequency; and (iv) the US intensity.

The impedance monitoring apparatus may feature transducers/sensors for measuring impedance, including transducers/sensors for measuring electrical impedance, transducers/sensors for measuring mechanical impedance, transducers/sensors for measuring body temperature, transducers/sensors for measuring impedance between electrical stimulation electrodes, transducers/sensors for measuring impedance between particular transducers/sensors, transducers/sensors for measuring impedance between the electrodes and particular transducers/sensors, transducers/sensors for measuring impedance by US diagnostics, transducers/sensors for measuring impedance by an imaging apparatus, and any combination thereof.

The controller may dynamically change the at least one parameter by:
(a) when the impedance is monitored above the impedance range, at least one of:
(1) reducing impedance by at least one of:
(i) increasing at least one of: the first electric intensity and the second electric intensity; and
(ii) reducing the interferential frequency by increasing frequency gap between the first electric frequency and the second electric frequency [by decreasing the lower frequency and/or increasing the higher frequency; and
(2) increasing US penetration depth by at least one of:
(i) decreasing the US frequency; and
(ii) increasing the US intensity; and
(b) when the impedance is monitored below the impedance range, at least one of:
(1) increasing the impedance by at least one of:
(i) reducing at least one of: the first electric intensity and the second electric intensity; and
(ii) increasing the interferential frequency by reducing frequency gap between the first electric frequency and the second electric frequency; and
(2) decreasing US penetration depth by at least one of:
(i) increasing the US frequency; and
(ii) decreasing the US intensity.

The controller may dynamically change another of the at least one parameter at a second pace, which is slower than the first pace at which the parameter is dynamically changed, wherein the intensity and frequency of the ultrasound waves are maintained within the ultrasound range, such that at least one pattern of resonant ultrasound waves is effected to momentarily reach the internal organ.

The controller may dynamically change the parameter by altering the ultrasound transmission by 3-30 sec per change, adding/taking power by 0.1 W/cm$^2$, increasing/decreasing frequency from 0.7 MHz to 3.5 MHz, or every 3-30 seconds, when changing power/frequency keeping frequency/power constant for 3 min. and vice versa. The controller may be configured to repeatedly dynamically change the parameter, several times in one session, or to dynamically change the parameter by cyclic alternation of the waves of a pair of electrodes between two opposed pairs of 4 electrodes, or by gradually changing the phase shift between two constant-frequency-waves having similar or slightly shifted frequencies.

The US apparatus may further include US diagnostics and/or imaging equipment for determining the region to be treated over the internal tissue/organ. The US diagnostics equipment may be combined with the ultrasound (US) appliance.

The interferential electrical stimulation apparatus may apply electrical stimulation at intensity in the electrical stimulation range of 1-70 mA. The US appliance may transmit ultrasound waves at intensity in the ultrasound range of 0.7 MHz-3.5 MHz, 0-2.1 Watt/cm$^2$.

The US apparatus may further include massaging equipment for massaging the treatment region simultaneously with the applying of interferential electrical stimulation and transmitting of the ultrasound waves, and gel for its application onto skin at the treatment region before transmitting the ultrasound waves.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

Figure 1:
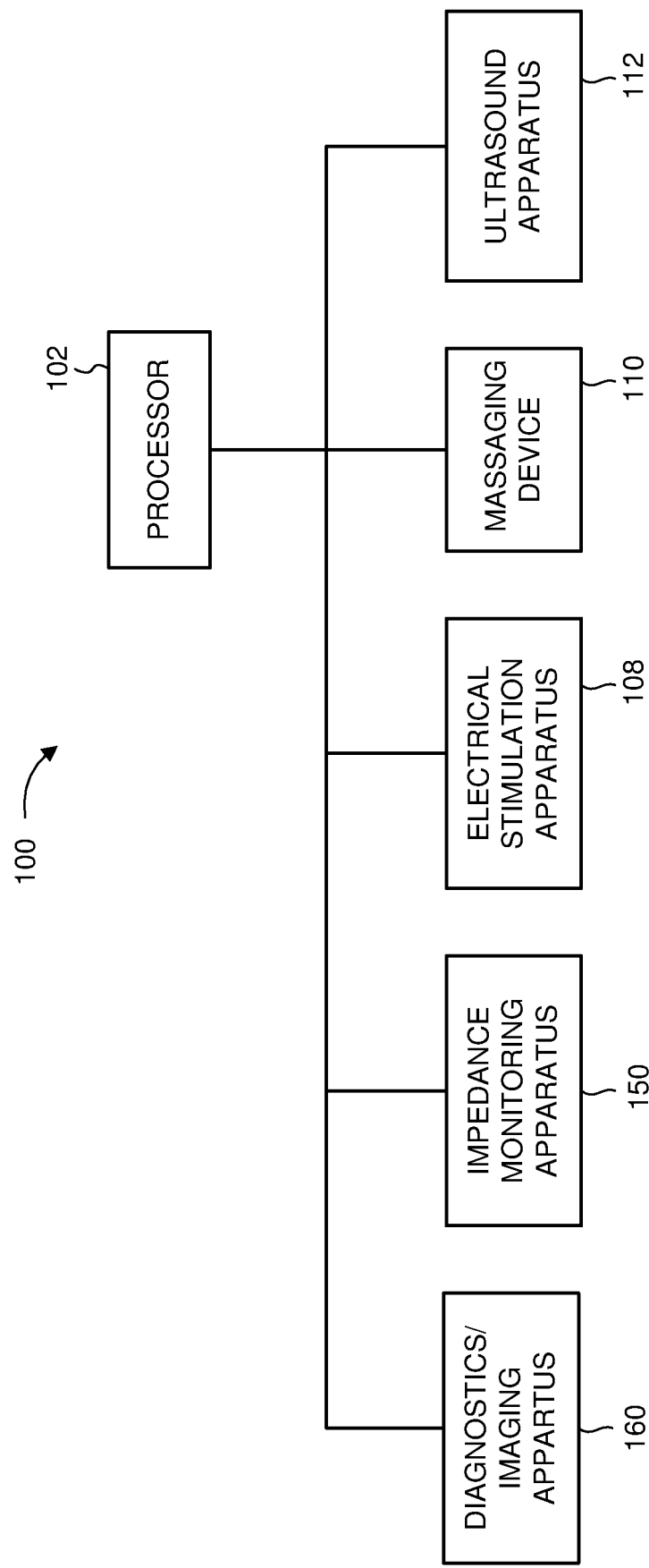
FIG. 1 is a block diagram of a system for inducing persistent mechanical and electrical impedances of the body tissue for facilitating effective conveyance of low energy ultrasound energy to a treated internal tissue or organ, constructed and operative in accordance with an embodiment of the disclosed technique.

The disclosed technique overcomes the disadvantages of the prior art by providing a novel system and method for inducing persistent mechanical and electrical impedances of the body tissue for facilitating effective conveyance of low energy ultrasound energy to the treated internal tissue, or organ. In particular, the novel system and method is operational for enhancing the fertility of female organs, and for treating ulcer, a closed wound, an internal injury, inflammation, and nerves. The system includes an ultrasound apparatus configured to transmit ultrasound waves, at a particular frequency range and intensity range, toward the treatment region. The ultrasound transmission induces the release of fluids and waste products in the underlying tissues, and their subsequent removal from the circulatory system, increasing blood flow and improves microcirculation at the treatment region. The system further includes an electrical stimulation apparatus for providing interferential electrical stimulation to the treatment region, simultaneously with the ultrasound transmission. The interferential electrical stimulation induces intermittent contractions of the muscle tissue at the treatment region, which applies repetitive pressure against the underlying tissues and associated vasculature from below the female fertility organ. the ulcer affected tissue, and nerves, promoting blood flow and improved circulation. An external massage may also be applied at the treatment region, such as by using a massaging device or manual manipulation, to further promote blood flow and improve circulatory and lymphatic operation in the region. Additional pressure may be exerted by kneading or pressing the ultrasound transducer against the treatment region.

The term "female fertility", and any variations thereof, as used herein refers to any type of female organs and their prospects to be successfully involved in insemination, conception, fertilization, impregnation and all the processes that consummate pregnancy, in a region of a female body. Accordingly, the disclosed technique is applicable for treating any type or form of female fertility, of any kind, or degree of severity.

The term "female fertility organ" and any variation thereof, as used herein, refers to organs involved in the female fertility processes, including, without limitation, organs such as ovarian follicle, blood vessel of the uterus (womb), ovary, endometrial lining, and Fallopian tube.

The term "internal organ" or "internal tissue" and any variation thereof, as used herein, refers to any organs, any internal tissue, including nerves, ulcer affected tissue, closed wounds, inflammation, and internal injuries.

The term "simultaneous", and any variations thereof, as used herein, also encompasses a period of time before, and a period of time after, the duration under consideration. Accordingly, a first procedure that is described as being performed "simultaneously" to a second procedure, may be performed, e.g., immediately before, immediately after, and/or during the second procedure.

In its broadest aspects, the disclosed technique concerns apparatus and method for applying low energy US while inducing impedance of the body tissue to be maintained within an impedance range for facilitating effective conveyance of low energy ultrasound waves onto an internal organ, internal tissue, inflammation, and nerves, to be treated by the ultrasound waves.

US Patent Application Publication No. 2013/289416 A1 (of the present inventor) discloses a system and method for treating skin ulcer, such as diabetic ulcer, on a treatment region of the body. The disclosure teaches application of interferential electric stimulation simultaneously with ultrasound energy. Operating parameters of the interferential electric stimulation, such as intensity, frequency, and pulse duration may be varied every few minutes over the course of treatment session in response to clinical feedback from the patient such as an indication of pain or discomfort, and the parameters of the electric stimulation may be further hopped or gradually changed, in an arbitrary manner or according to a predetermined pattern, to prevent the body from adapting to the applied electrical stimulation. However, clinical feedback from the patient do not indicate how effective treatment is, and which parameters should be changed and how, for enhancing the effectiveness. Changing of parameters in an arbitrary manner or a predetermined pattern are not apt to follow the actual response of the body in real time and are either random or based on models of an expected response, thus do not necessarily provide the essential change which is required to prevent body adaptation. Publication No. 2013/289416 A1 concern skin ulcers, which involves the treatment of topical tissues, which are proximate to the ultrasound and electric energy sources, while deeper healthy tissue receives only a fraction of the energy and thus is not substantially exposed to undesired effects. The present application is directed at treating internal tissue and organs requiring the unwelcome penetration of intense energy through healthy tissue which absorbs some of the energy, while only unabsorbed energy reaches the internal tissue to be treated. The present invention takes into account that body adaptation leads to increase of mechanical impedance which is inhibits the passage of ultrasound energy to the internal organ through body tissue in the path of energy propagation and hampers effectiveness of treatment at the optimal ultrasound intensity energy, requiring undesirable increase of ultrasound intensity which is often damaging to the topical and intermediate interfering tissues in the path of propagation. Reduction of treatment energy to levels which are far from inflicting damage to topical and intermediate tissue may end up with ineffective energy levels due to attenuation by the topical and intermediate tissue. This inadvisable effect is prominent upon treatment of in internal organ, such as an internal closed wound, internal ulcer, internal injury or inflammation, particularly of diabetic background, and treating an internal female fertility organ for enhancing female fertility. Electrical "impedance" customarily includes "resistance" and "reactance", and its measurement can be achieved by several methods. Although mechanical impedance can be detected directly, as this impedance is correlated to electrical impedance, it may be practical to detect the electrical impedance instead. The present invention seeks to detect, measure and monitor this impedance along the course of treatment session, and, in response, continuously change parameters of electrical stimulation and/or ultrasound energy, such that the monitored impedance will undergo continuous reclamation of any deviation for maintaining the impedance within a desired range. Keeping the impedance in a desired range is a practical object rather than keeping the impedance as low as possible, because the body always and continuously adapts to an effective treatment, and because low impedance can be achieved at treatment energies which are not necessarily effective. In experiments mentioned below, at 50 Hz (faradic current of electrical stimulation) the impedance for a skin area of 100 cm$^2$ was found to be approximately 3000Ω. At 4000 Hz (medium frequency) the skin impedance of the same area drops to around 50Ω. Skin impedance of 500Ω for example is acceptable for an effective treatment and a working range impedance may be selected thereabout.

Low skin impedance allows a lower ultrasound (and electric stimulating) energy to be applied and penetrate the outer tissue layers and reach the treated internal tissue or organ. This medium frequency dwells, however, well outside the normal biologically responsive frequency range of 0.1 Hz to 250 Hz. The changes of treatment parameters may be selected and applied along the course of the treatment session in response to changes in impedance, after an initial calibration treatment in which changes are applied in a random, arbitrary, or by a predetermined pattern, and as the reaction of the body leading to increase or decrease of impedance outside the desired range is detected, those changes of parameters that were found to induce reversal of body response for reclamation of any deviation from the desired impedance range.

The US apparatus includes a non-invasive US appliance used on a treatment region over the internal organ or tissue, and an electrical stimulation apparatus for simultaneously inducing interferential electrical stimulation. A controller controls parameters of the electrical stimulation apparatus and the US appliance, and dynamically changes at least one of the parameters, for maintaining the impedance of the body tissue in the treatment region within an impedance range. Preferably, the US apparatus includes an impedance monitor for continuously detecting, measuring and monitoring electrical impedance in the treatment region, wherein the controller dynamically changes at least one of the parameter in response to the electrical impedance as monitored, for maintaining the impedance within the predefined range. The impedance monitor may feature electrical impedance sensors which are located over the body in or in the vicinity of the treatment area, or indirect sensors such as a thermal sensor overlooking the treatment area. Direct measurement of mechanical impedance may be carried out for example by the ultrasound sensor(s) similar to those used for ultrasound diagnosis (by calculating transmitted, echoed, dissipated or dispersed ultrasound energy). Further means for detecting and dynamically tracking electrical impedance may involve application of other electromagnetic ranges, (e.g., RF) which allow detection of transmission, dissipation, and dispersion within the body.

Some contemporary techniques which are in use for assessing body fat can provide the impedance assessment and tracking to be applied for the purposes of the present invention—which seeks to detect the impedance of local layers only and is therefore even simpler to apply. Available technologies include, for example, Bioelectrical Impedance Analysis (BIA), Bio-impedance Spectroscopy (BIS), and Electrical Impedance Myography (EIM), wherein the elected technology is applied by injecting electrical currents into small body regions in or in the vicinity of the treatment region.

An internal organ or tissue cannot be effectively treated by non-invasive ultrasound procedure in a manner similar to the treatment of external organs or similarly proximate to the ultrasound head (e.g., the skin, subcutaneous tissue, disposed right behind the subcutaneous tissue, an exposed tissue, tissue proximate to an invasive ultrasound head penetrating internally inside the body). The massive tissues separating between the ultrasound head and the internal organ/tissue to be treated absorbs and dissipates the ultrasound waves, thereby frustrating the treatment. Increasing ultrasound power, by applying high energy ultrasound waves so that eventually sufficiently energetic waves would reach the internal organ or tissue, would result in serious damage to the separating tissues.

The invention is also applicable to treating any internal tissue, such as of a closed wound, internal injury, internal inflammation, and ulcer.

It is noted that diabetes often involves closed internal wounds, inflammation and ulcers, typically in peripheral organs such as toes, fingers, and limbs, due to congestion of peripheral capillary blood vessels, whose blocking denies blood supply and essential nutrition of the effected tissue. Such wounds typically concern damage to the nerve cells, developing at phases which sometimes also indicate the progression of ulcer. Peripheral neuropathic pain often occurs as a precursor of ulcers. Further damage to the nerves is often followed by neuropathic and nociceptive pain, which accompany injury of tissue and nerves. Further tissue damage is typically accompanied by numbness or anesthesia, and further damage results in diabetic ulcers, appearing sometimes as an internal closed wound, which may further develop into an open wound, bacterial infection and may eventually result with amputation of the peripheral organ as a life saving measure.

Accordingly, the damage to the nerves deserves tracking in particular. Nerves include neurons (or nerve cells), with central nucleus surrounded by the soma, branching dendrites, peripherally projecting axons wrapped by myelin sheath, and further peripherally extending axon terminals. Damage to nucleus is irreparable, while injury of axons, axon terminals, dendrites and perhaps myelin sheath can be rehabilitated, at least to some extent. Typical diabetic damage to the nerves begins with damage to axon terminals resulting by neuropathic pain. Further damage to myelin sheath leads to damage of the sheathed axons, resulting by Nausea pain. Further damage to axons, and damage to dendrites results with numbness and further damage thereto as well as damage of the nucleus, results with anesthesia.

The invention is directed at treating developing ulcer, particularly of diabetic background, including treating the nerves which are affected by diabetes and deserve rehabilitation on their own, and whose status is also indicative of the progression and regression of diabetic ulcer. The treatment of nerves is mainly directed at rehabilitating axon terminals, but may also extend to treating axons, myelin, and dendrites.

Furthermore, under chronic inflammation, cells secrete prostaglandins and other chemicals that migrate to the nerve receptors by a process known as chemotaxis. These chemicals activate the nerves to trigger pain. Reducing inflammation hinders release of these chemicals and thereby averts pain.

One major factor that determines the amount of energy absorbed by the separating tissues is the mechanical impedance of the separating tissues. Mechanical impedance of the body tissue is correlated to electrical impedance of the body tissue—which can be manipulated. The body tissue, when exposed to electrical stimulation, tend to adapt and gradually develop an increased resistance which results in increased mechanical impedance (and increased electrical impedance). The novel method induces persistent mechanical impedance of the body tissue, by applying dynamically changing manipulation of electrical stimulation to the region of treatment, which prevails the natural adaption of the body tissue to the electrical stimulation as experienced by the body tissue.

For example, in order to overcome the acclimatization of the skin impedance, increasing the electric stimulation voltage can be used to achieve the desired stimulation current, but the patient will usually experience a less comfortable treatment. The penetration depth of such a current may be poor and may, at least partially, be limited by the discomfort of the patient.

Experimental measurements carried out at stimulation frequency of 50 Hz, resulted with an impedance for a 100 $cm^2$ of skin at approximately 3000 Ohms ($\Omega$). At 4000 Hz (medium frequency) the skin impedance of the same area was around 50 Ohms.

These measurements suggest that much lower stimulation voltages can be used to produce the desired stimulation current, while resulting in less skin sensitivity and a more comfortable treatment experience to the patient. This medium frequency is however, well beyond the normal biologically effective frequency range (0.1 to 250 Hz) in which the body or skin tissue effectively reacts.

In order to produce the required stimulation, two medium frequencies are applied. A constant frequency of, say, 4000 Hz is applied to one pair of electrodes and a slightly different frequency of, say, 3900 Hz is applied to the other pair. These two frequencies 'interfere' to produce an amplitude modulated medium frequency (beat frequency) in the tissue. The tissue reacts in response to the cyclic rise and fall of the current intensity. It is the amplitude modulation frequency (AMF) that is within the normal biologically effective frequency range and not the medium frequency (carrier).

Nevertheless, only specific ultrasound waves are effective or having the right "resonance" to effectively treat the internal organ, without damaging the organ, namely—within an energy range above a minimal effective threshold and below a damaging threshold. To that end, the ultrasound waves are manipulated to be applied in a dynamically changing pattern, to ensure that the appropriate effective waves are eventually applied to the treated internal organ or tissue.

Figure 2:
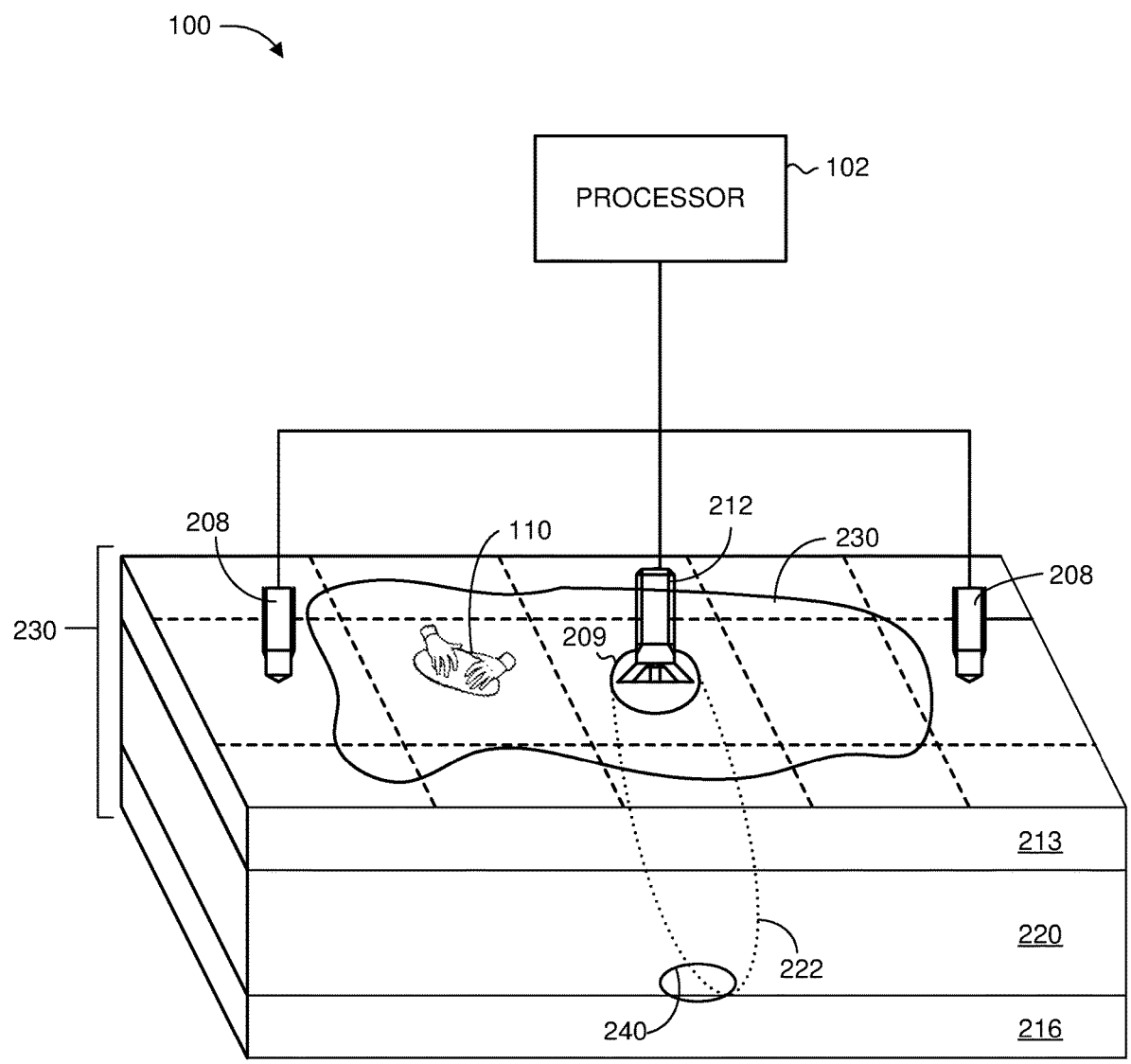
FIG. 2 is a schematic illustration of the system of FIG. 1 treating a body region of a patient, in accordance with an embodiment of the disclosed technique, without impedance monitoring apparatus which is described with reference to FIG. 6.

Reference is now made to FIGS. 1 and 2. FIG. 1 is a block diagram of an embodiment of a system, generally referenced 100, for treating internal tissue, inflammation or enhancing fertility of female organs, constructed and operative in accordance with an embodiment of the disclosed technique. FIG. 2 is a schematic illustration of the system of FIG. 1 treating a body region of a patient, in accordance with an embodiment of the disclosed technique. System 100 includes processor 102, ultrasound apparatus 112, electrical stimulation apparatus 108, impedance monitoring apparatus 150, diagnostics/imaging equipment 160, and massaging device 110. Processor 102 is coupled with electrical stimulation apparatus 108, with impedance tracking and monitoring apparatus 150, with diagnostics/imaging equipment 160, with massaging device 110, and with ultrasound apparatus 112. Electrical stimulation apparatus 108 includes electrodes 208. Ultrasound apparatus 112 typically includes a signal generator unit (not shown) and an ultrasound transducer 212. Impedance monitoring apparatus 150 includes impedance transducers/sensors and/or thermal sensors as further elaborated with reference to elements such as electrodes 611, transducers/sensors 651, 652, 656, 662 and monitor 654 of FIG. 6). Processor 102 is operative to control and manage the operations of electrical stimulation apparatus 108, massaging device 110, and ultrasound apparatus 112. Processor 102 may be partially or fully embodied by any form of hardware, software, or a combination thereof, and may be at least partially embodied by a hardware or software component that is integrated with any one of: electrical stimulation apparatus 108, massaging device 110, and ultrasound apparatus 112.

Referring to FIG. 2, system 100 is applied to a treatment region 230 on the body of a patient, where treatment region 230 is located above internal tissue/organ 240 that requires treatment. Internal tissue/organ 240 may be female fertility organ (e.g., the ovarian follicle, a blood vessel of the uterus (womb), the ovary, the endometrial lining, and/or the Fallopian tube). or any other internal organ, tissue, including internal ulcer, a closed wound, an internal injury, nerves, or inflammation—including any parts thereof, and any other internally disposed living body tissue. Treatment region 230 includes a skin tissue layer 213 (i.e., epidermis, dermis, and hypodermis), a fat tissue layer 220 (i.e., subcutaneous fat), and a muscle tissue layer 216. Internal tissue/organ 240 is disposed deep below into the skin tissue layer 213, fat tissue layer 220, and muscle tissue layer 216.

Electrodes 208 are positioned onto the patient at treatment region 230 in proximity to internal tissue/organ 240. Stimulation apparatus 108 applies interferential electrical stimulation to treatment region 230 via electrodes 208. The electrical stimulation reaches muscle tissue 216 and produces stimulation action above internal tissue/organ 240 while stimulating blood circulation in the area. Electrodes 208 may be adhered or otherwise fixedly positioned directly onto skin layer 213, such that electrodes 208 remain stationary during treatment. Alternatively, one or more of electrodes 208 may be integrated with the interfacing head of ultrasound transducer 212 such that electrodes 208 are operated in conjunction with the electrode within the interfacing head transducer 212, which is moved by the operator over treatment region 230.

Ultrasound transducer 212 transmits ultrasound waves toward treatment region 230. A gel 209 is optionally applied to the treatment region, to enhance the penetration of the ultrasound waves, as elaborated upon hereinbelow. The transmitted ultrasound waves penetrate skin tissue layer 213 and fat tissue layer 220. The intensity and/or frequency of the transmitted ultrasound waves may be selected so that the ultrasound waves, which are attenuated while propagating through layers 213, 220, and 216. In particular, the ultrasound waves penetrate into muscle tissue layer 216. A typical cross-section of effective ultrasound penetration in accordance with the disclosed technique is represented by perforated lines 222. In general, the transmitted ultrasound waves function to sufficiently stimulate blood circulation in the tissue layers of treatment region 130, thereby promoting the healing of internal tissue/organ 240. Ultrasound transducer 212 is preferably operative to knead or press against the skin at treatment region 230 during the operation of ultrasound apparatus 112. Massaging device 110 massages treatment region 230, preferably simultaneously with the electrical stimulation and the ultrasound transmission.

Figure 3:
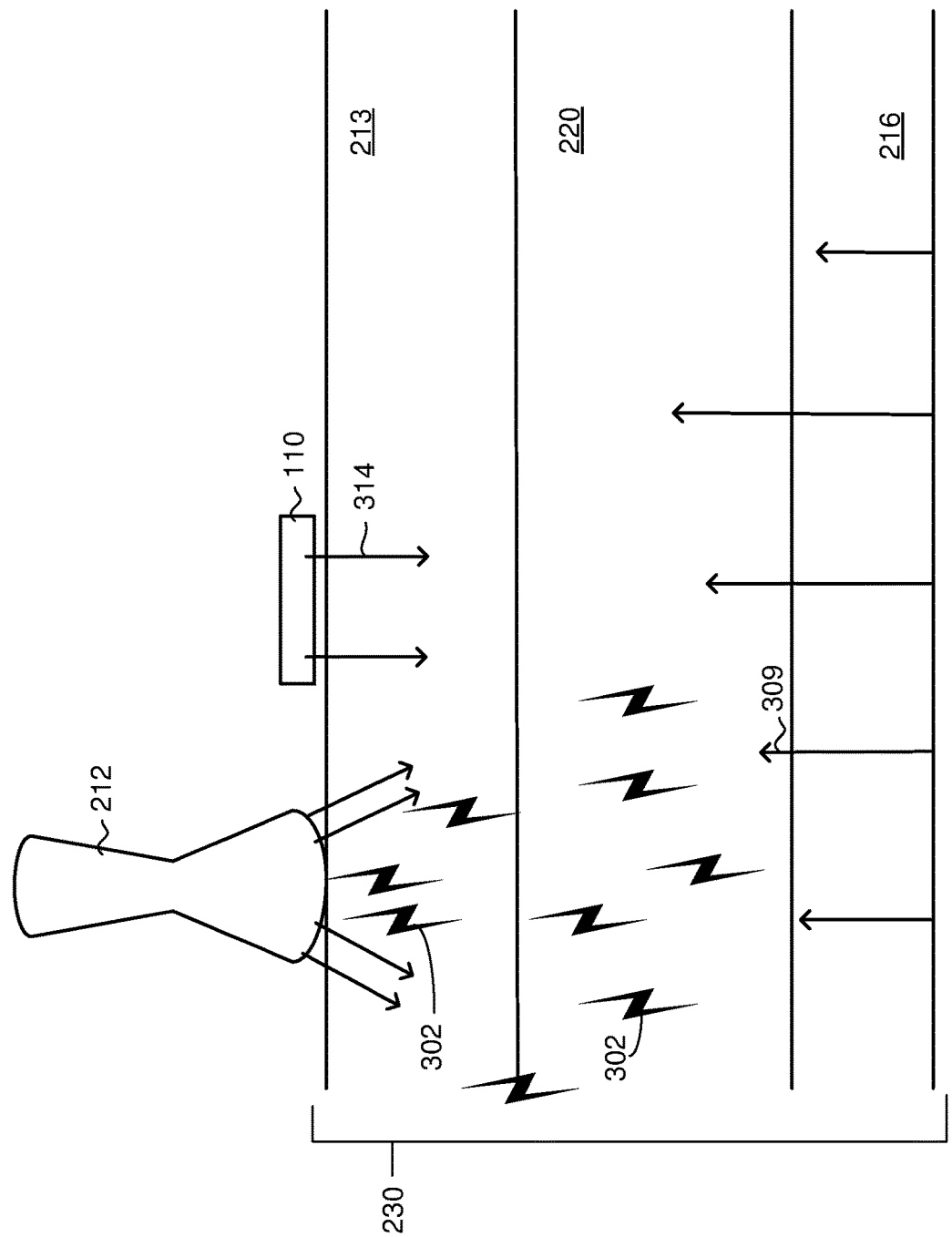
FIG. 3 is a schematic illustration of physical and biological processes that occur during the application of the disclosed technique.

Reference is now made to FIG. 3, which is a schematic illustration of physical and biological processes that occur during the application of the disclosed technique. Ultrasound transducer 212 transmits ultrasound waves 302 toward treatment region 230. Ultrasound waves are very high frequency sound waves (i.e., above approximately 20 KHz) that create changes in the density and pressure of the medium through which the waves propagate. Ultrasound waves are longitudinal waves made up of high pressure regions ("compression") and low pressure regions ("rarefaction"). When an ultrasound wave strikes a material, the particles of that material begin to oscillate and gradually generate heat. Thus, kinetic energy from the ultrasound wave is transferred into thermal energy in the impacted material.

One effect of the ultrasound transmission is to improve microcirculation (i.e., the blood circulation through the microvascular network that is responsible for the distribution of blood within tissues) in the treatment region. As ultrasound waves 302 propagate through skin tissue layer 213 and fat tissue layer 220, the resultant oscillation and softening of the tissues generates heat and pressure, which induces the release and subsequent removal of fluids and waste products stored in the tissue, while also enhancing blood flow and circulation in the region.

In accordance with the disclosed technique, ultrasound transducer 212 emits ultrasound waves 302 at a frequency between approximately 1-4 MHz, preferably from 0.7 MHz to 3.5 MHz and at intensities varying between approximately 0-2.5 W/cm$^2$, preferably between 0.5-2.1 W/cm$^2$, further preferably between 1-2.1 W/cm$^2$, and yet further preferably at approximately 1.8-2.1 W/cm$^2$. At these operating ranges, it is conjectured that microcirculation improvement takes place in the tissue in proximity to the internal organ/tissue 240, while healthy tissues on the path from the US head, such as muscles, remain unharmed. The ultrasound operating frequency or operating intensity may be varied over the course of a treatment session. Varying the operating frequency allows targeting of different depths in treatment region 230. Particularly, higher frequencies may be used to reach shallower tissue layers, whereas lower frequencies may be used to reach deeper tissue layers. When varying the frequency with regards to the depth of region being targeted, a first depth is preferably first treated completely, followed by the treatment of a second depth. The ultrasound intensity may be varied independent of the ultrasound frequency. Preferably, the operating frequency of ultrasound transducer 212 remains between 0.7-3.5 MHz, and the operating intensity of ultrasound transducer 212 remains between 0-2.1 W/cm$^2$. Different frequency/intensity combinations (e.g., high frequency and high intensity, low frequency and low intensity, high frequency and low intensity, low frequency and high intensity) may be applied in order to produce a desired effect and/or to penetrate a desired depth of the treatment region.

The treatment provider preferably utilizes feedback from the patient while the treatment is taking place, and proceeds to adjust the treatment if necessary. For example, the transmitted ultrasound waves are applied at a specific intensity until the patient experiences pain or can no longer endure the pain. If the patient indicates that he/she is experiencing pain or discomfort, the treatment provider may reduce the ultrasound intensity, reposition the ultrasound transducer onto a different portion of the treatment region, and/or change the ultrasound frequency in order to reach a different depth of the treatment region. With reference to the embodiment of FIG. 6, the above-mentioned adjustments are performed on top of the continually changing of ultrasound or stimulation parameters which are performed with the embodiment of FIG. 6, preferably automatically, in response to the tracked changes of body impedance, for sake of keeping impedance in a desired range.

Figure 4A:
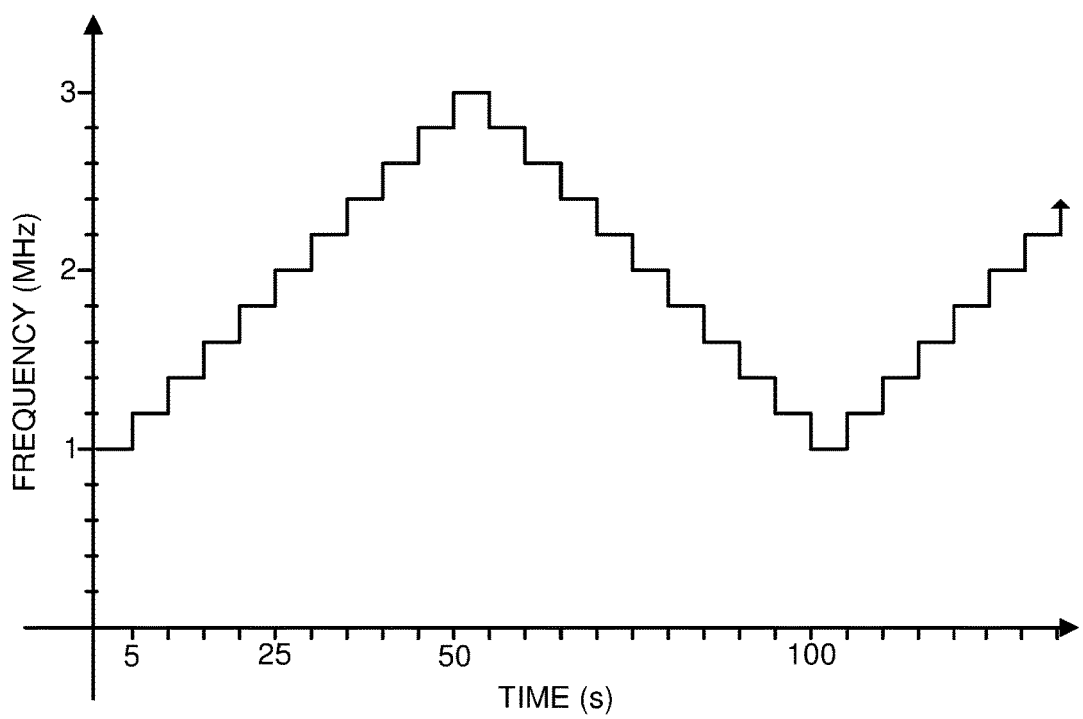
FIG. 4A is a graph that depicts a first exemplary variation of ultrasound frequency as a function of time, in accordance with an embodiment of the disclosed technique.
Figure 4B:
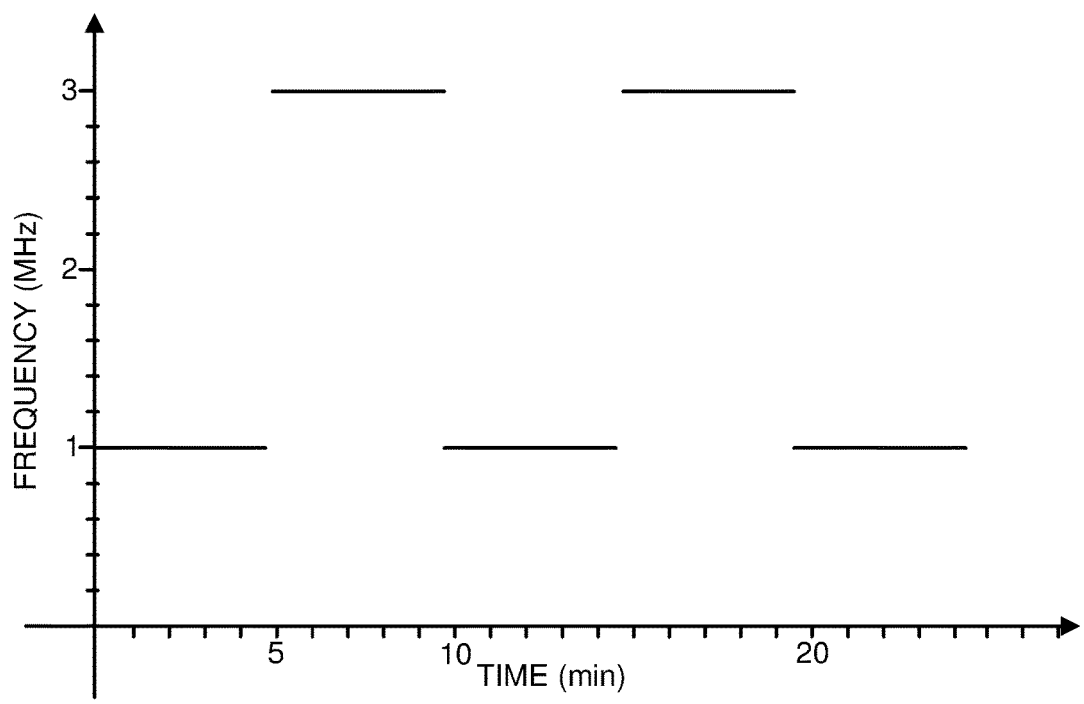
FIG. 4B is a graph that depicts a second exemplary variation of ultrasound frequency as a function of time, in accordance with an embodiment of the disclosed technique.

Reference is now made to FIGS. 4A and 4B. FIG. 4A is a graph that depicts a first exemplary variation of ultrasound frequency as a function of time, in accordance with an embodiment of the disclosed technique. FIG. 4B is a graph that depicts a second exemplary variation of ultrasound frequency as a function of time, in accordance with an embodiment of the disclosed technique. Referring to FIG. 4A, the frequency can be altered over the course of the treatment from 0.7 MHz to 3.5 MHz and back again to 1 MHz, cyclically, at 200 KHz increments lasting 5 seconds. The increments may alternatively be shorter or longer time periods, for example 3 seconds or 10 seconds, and may alternatively be larger or smaller frequencies, for example 100 KHz or 500 KHz. Referring to FIG. 4B, the frequency can also be altered sharply, in a stepwise manner, between 0.7 MHz and 3.5 MHz and back again to 0.7 MHz, cyclically, where a particular frequency is applied for 5 minutes. The duration of the applied frequency may alternatively be a shorter or longer time period, for example 3 minutes, 10 minutes, or 20 minutes.

Referring back to FIGS. 1 and 2, stimulation apparatus 108 applies interferential electrical stimulation to treatment region 230, inducing intermittent contractions of muscle tissue layer 216. Electrodes 208 are attached to skin tissue layer 213 with the aid of attaching means, such as adhesive patches, at the beginning and end of the muscle fibers that cross treatment region 230. Typically, at least two pairs of electrodes 208 are employed to generate interferential beat frequencies, as will be discussed further hereinbelow. Interferential current is applied to treatment region 230 via electrodes 208 at frequencies ranging from 5-150 Hz resultant beat frequency, which stimulates intermittent contractions of the muscle tissue. These contractions create a tense bedding of muscle against fat tissue layer 220 and skin tissue layer 213 around internal tissue/organ 240, providing an opposing force against the treated surface tissue. The rapid contraction-relaxation motion of the muscles (represented by pressure arrows 309 in FIG. 3) applies repetitive pressure against skin tissue 213 and fat tissue 220 and the associated vasculature, promoting blood flow and improved circulation in the vicinity of internal tissue/organ 240. The interferential electrical stimulation is applied simultaneously with the transmission of ultrasound waves by ultrasound apparatus 112, thereby further augmenting the circulation improvement induced by the ultrasound. It is believed that a periodic application of pressure pulses with alternating relief intermissions is preferred to a constant pressure application with respect to the tenability of living organic tissue, especially in circumstances of force accompanying an aggressive treatment. Accordingly, interferential electrical stimulation has been found to be effective for at least half an hour after an intensive ultrasound treatment, in accordance with the disclosed technique.

The operating parameters of the interferential electrical stimulation (e.g., intensity, frequency, pulse duration) may be varied over the course of a treatment session, such as in response to clinical feedback (e.g., an indication of pain or discomfort) from the patient. The operating intensity of the electrical stimulation is preferably between 1-70 mA. The interferential electrical stimulation is performed using interferential isoplanar (4 poles) and interferential vectorial (4 poles) stimulation techniques, or combinations thereof. The interferential technique uses two alternating currents originating at different channels, each at slightly different carrier frequencies. The currents coincide at treatment region 230 and create interference (constructive or destructive), producing a resultant beat frequency equal to the difference between the actual frequencies provided by each pair of electrodes. For example, a frequency of 100 Hz is yielded by 3,900 Hz in one electrode pair and 4,000 Hz in the other electrode pair. Accordingly, the resultant wave is a 3,900-4,000 Hz carrier wave modulated at an envelope amplitude frequency of 100 Hz. The dominant carrier frequency depends on the geometrical locations of the electrodes. Interferential stimulation is almost exclusively delivered using a quadripolar technique, in which four independent pads are arranged in such a way as to achieve the desired effect. Typically, two pairs of electrodes are positioned around the treatment region, with each pair perpendicular to the other. The premodulated technique involves superimposing a signal with the effective frequency onto a continuously transmitted carrier wave, for instance, a 4000 Hz carrier wave modulated at an envelope amplitude frequency of 100 Hz. It is noted that multiple electrical stimulation techniques can be used, in various combinations, in various orders, and with various intermission durations (in between different electrical stimulation techniques), in accordance with the disclosed technique. For example, the electrical stimulation may include applying an interferential technique initially for 10 minutes, then switching to a premodulated technique for an additional 5 minutes, then switching back to an interferential technique for another 10 minutes, then cycling back through this process again. While each interferential electrical stimulation technique is applied, the carrier wave frequency is preferably changed (hopped) at least once, thus preventing the body from adapting to the applied electrical stimulation (and consequently ceasing to react with intermittent muscle contractions), and avoiding the need to increase the operating intensity. For example, while each interferential electrical stimulation technique is applied, the carrier wave may be hopped from a 4,000 Hz carrier wave to a 2,400-2,500 Hz carrier wave. Similarly, the envelope or beat frequency (where relevant) is changed gradually or hopped between selected frequencies.

Figure 6:
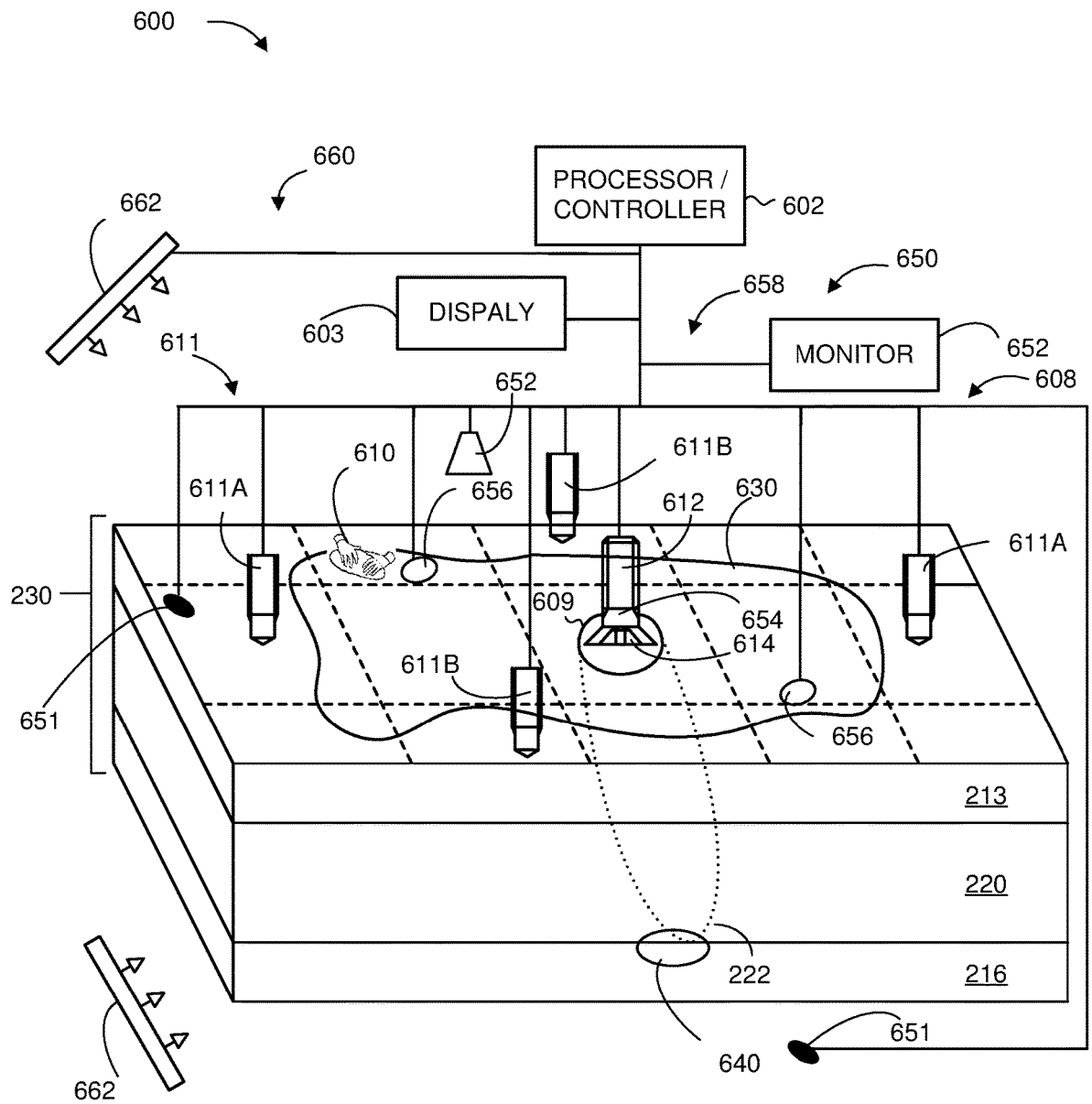
FIG. 6 illustrates system 600 for inducing persistent mechanical and electrical impedances of the body tissue for facilitating effective conveyance of low energy ultrasound energy to a treated internal tissue or organ, constructed and operative in accordance with one embodiment of the invention.

During the initial treatment session, it is preferable to use low current intensities in the range of approximately 1-5 mA, as a higher current intensity may agitate or alarm an inexperienced patient. In more advanced treatments, it is possible to apply the more effective higher current intensities in the range of approximately 1-70 mA. Patient feedback may be utilized by the treatment provider for adapting the operating intensity as necessary. The effective frequencies are between approximately 5-150 Hz. It is noted that intermittent muscle contractions may not occur when applying interferential electrical stimulation at operating frequencies above a certain level (e.g., approximately 250 Hz). At higher frequencies, the vibrations are so frequent that the muscles can remain constantly tense, whereas at lower frequencies the vibrations are slower but much stronger. Since the muscle adapts to a specific frequency, it is advisable to alter the operating frequency of the electrical stimulation throughout the duration of the treatment session, and even during the application of a particular stimulation technique. The operating frequency may be altered in an arbitrary manner, or in accordance with a predetermined pattern, such as: (1) applying a first frequency for a fixed amount of time before switching to a second frequency; (2) gradually changing frequencies from a first frequency to a second frequency, such as switching from 5 Hz to 150 Hz and back (e.g., in a sinusoidal cycle); (3) similar to pattern (2), but remaining for a longer duration (such as 1 second) at the extreme levels; (4) applying only the extreme frequencies intermittently. Other patterns for altering the operating frequency may also be employed. With reference to FIG. 6, any and all of mentioned altering action may be performed, preferably automatically, in response to changes in body impedance as tracked by body impedance monitoring means of the embodiment of FIG. 6, for the sake of keeping impedance in a desired range.

Referring again to FIGS. 1 to 4, Various operating parameters of the interferential electrical stimulation, such as: the frequency, amplitude modulated frequency, spectrum, rotation, emission, and pause parameters, are adjustable. The "frequency" parameter allows the operating frequency to be set between two available values (e.g., 2500 Hz or 4800 Hz) for each alternating current. The selection of the frequency value is crucial, since the interferential current penetrates more easily at a higher current frequency. The "amplitude modulated frequency (AMF)" can be chosen such that the basic value of the low frequency modulation can be set as needed. For example, the AMF parameter can be set to 100 Hz, but can be adjusted from 1 Hz to 100 Hz, with 1 Hz step intervals. The "spectrum" parameter can be used to adjust the AMF value, and is adjustable from 0 to 100 Hz, with 1 Hz step intervals. For example, at a setting of 100 Hz AMF and 50 Hz spectrum, the AMF will increase in the tissue from 100 Hz to 150 Hz and return again to 100 Hz. The spectrum parameter is used in order to avoid assuefaction symptoms. For the interferential vectorial technique, a quadripolar interferential current is employed, but the direction of the stimulation is the same as in the bipolar technique. Therefore, at a certain moment, the current is activated by only two diagonal electrodes. The tissue stimulation therefore rotates automatically between the electrodes. The "rotation" parameter can be used to manually adjust the rotation speed of the vector. The rotation parameter is usually assigned an arbitrary value between 1 and 100. The "emission" parameter allows for the adjustment of the stimulation length. The "pause" parameter enables the stimulation to be paused if necessary.

If the frequency or intensity of the interferential electrical stimulation is varied rapidly, then the frequency of the ultrasound transmission is preferably varied slowly. Conversely, if the frequency or intensity of the interferential electrical stimulation is varied slowly, then the frequency of the ultrasound transmission is preferably varied rapidly. In other words, it is suggested that the rate of varying the parameters related to the interferential electrical stimulation be inversely proportional to the rate of varying the parameters related to the ultrasound transmission.

Figure 5A:
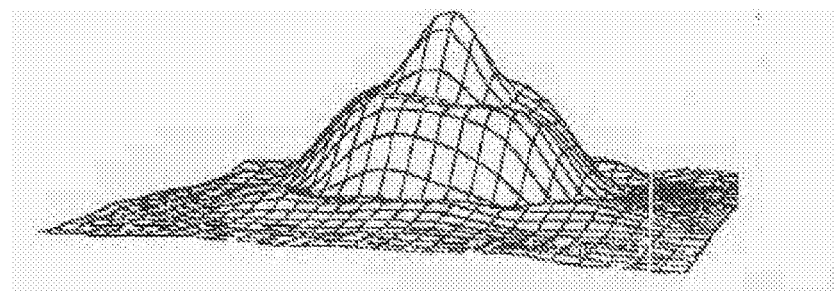
FIGS. 5A and 5B are three-dimensional graphical illustrations depicting the mountain-like morphing of tissues resulting from the synergy between interferential electrical stimulation and ultrasound waves applied to the treatment region, in accordance with an embodiment of the disclosed technique.
Figure 5B:
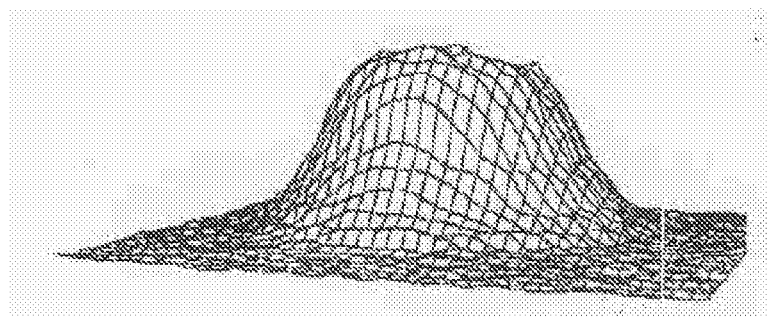

Reference is now made to FIGS. 5A and 5B, which are three-dimensional graphical illustrations depicting the mountain-like morphing of tissues resulting from the synergy between interferential electrical stimulation and ultrasound waves applied to the treatment region. The illustrations of FIGS. 5A and 5B are provided as examples of two stationary states between which the effected body tissue transitions. These morphologies and transitions result from intensity differential gradients that occur through the synergy between the altering interferential electrical stimulation and the transmitted ultrasound waves. When this synergy is applied beneath and around the treatment region, it provides physical and thermal stimulation with improved microcirculation in proximity to the female fertility organ, thus significantly assisting the body in healing the internal tissue/organ, which may be a female fertility organ, ulcer, injury, wound, inflammation, and/or nerves.

Referring back to FIGS. 1 and 2, during a treatment session in accordance with the disclosed technique, the treatment provider slowly, gradually and gently moves ultrasound transducer 212 over treatment region 230, while preferably gently executing small circular massaging motions with transducer 212. It is noted that the action of the treatment provider may be automated, such as by using a robot or machine. Ultrasound transducer 212 is forcefully but carefully applied to treatment region 230 to generate substantial pressure. It is noted that it is important to be gentle and attentive to any pain or discomfort experienced by the patient, as treatment region 230 may be very sensitive. The treatment provider may optionally provide local or systemic sedatives, in order to alleviate pain for the patient. Ultrasound transducer 212 is preferably designed to allow both a forceful massage action and the penetration of ultrasound waves 302 into the underlying tissue at treatment region 230. Preferably, the massaging action and forceful pressure applied to treatment region 230 by ultrasound transducer 212 is interspersed with periodic intermissions. Ultrasound transducer 212 may be tilted in different directions (e.g., left, right, front and back) over the course of the massaging. This is achieved by tilting and moving the wrist in different directions repetitively, for example left-right-left, front-back-front, and left-front-right-back (i.e., a circular motion using the wrist as opposed to a circular motion using the arm). In this manner, ultrasound waves 302 penetrate deeper into treatment region 230, as the surface area of the head of ultrasound transducer 212 in contact with the skin is made smaller by the tilting. The kneading motion, together with the pressure applied to the treatment region 230 by the head of transducer 210, presses and squeezes against the vasculature in the underlying tissues. For example, small circular massage motions can be interspersed with left-right-left tilting massage motions, or any combination of the above-mentioned massage techniques, or other massage techniques known in the art. It is noted that the kneading action or the pressure exertion of the ultrasound transducer in accordance with the disclosed technique deviates from the general practice of ultrasound transmission for medical applications, which discourages any forceful contact between the ultrasound transducer and the skin.

A further measure to exert pressure on the treatment region is via a manual and/or mechanical external massage, such as by using massaging device 110. A practical and simple type of massage is the mere massaging by the bare hands of a treating person. However, various types of massaging tools or equipment are also applicable. Referring to FIG. 3, the massage applies pressure (as represented by arrows 314) against treatment region 230, thereby squeezing the skin surface and promoting blood flow to the area and improving the circulation and lymphatic network. Preferably, the massaging action is applied to the exact area of treatment region 230 on which ultrasound waves 320 are directed, simultaneously to the ultrasound transmission. The massage may be applied effectively during the ultrasound transmission or for a while thereafter.

According to another aspect of the disclosed technique, a gel 209 is rubbed onto skin layer 213 at treatment region 230 prior to the ultrasound transmission. Gel 209 is preferably water-based, to conform to the ultrasound conductive medium. Preferable gels can include ingredients such as: hydroxyl acids, plant extracts, wheat proteins, macadamia oil, chamomile, zinc, salicylic acid, and caffeine. Gel 209 has several purposes. Firstly, gel 209 effectively conducts ultrasound waves 302 between the ultrasound transducer 212 and the tissues at treatment region 230. Gel 209 is also designed to provide smooth penetration of the ultrasound waves 302 to the underlying tissues. In addition, gel 209 lubricates the skin and prevents friction and scrapes to the skin, especially in circumstances where the head of ultrasound transducer 212 is forcefully pressed or kneaded against treatment region 330. Also, drugs, active ingredients and antiseptics, if added to gel 209, are absorbed into and/or disinfect the epidermis layer (of skin tissue 213) more effectively because of ultrasound waves 302, the heated fluids and tissue material, and the appearance of ruptures or cracks in treatment region 230. This absorption is further enhanced by the head of ultrasound transducer 212 forcefully rubbing gel 209 against the skin. The drugs or active ingredients that are absorbed may promote blood flow and circulation and provide the skin tissue with various beneficial minerals and nutrients. Throughout the course of the treatment session, the massaging action involved in rubbing gel 209 onto the skin also serves to improve circulation and the operation of the lymphatic system at the treatment region 230.

The application of one or any combination of any of the pressure increasing measures detailed hereinabove (i.e., ultrasound wave transmission, ultrasound transducer kneading, interferential electrical stimulation, and external massaging), can exert sufficient and suitable pressure on treatment region 230 from opposite directions (e.g., from above and below the treatment region if the patient is in a supine position), which that contributes to an effective treatment. It was found that the more (and preferably all) of the pressure increasing measures that are applied, the more substantial and irrefutable are the improvement in blood flow and circulation. The ultrasound transducer kneading, the interferential electrical stimulation, and the external massage are preferably applied simultaneously with the ultrasound transmission.

It is appreciated that the improvement in blood flow resulting from the treatment of the disclosed technique also generally improves the circulatory system and metabolism processes at the treatment region. Due to the softening of tissues, the arteries and capillaries within these tissues become widened (i.e., vasodilation). Circulation is then accelerated, and the tissues receive more oxygen and nutrients. As a result, the circulatory system and lymphatic system reach healthier states.

Ultrasound apparatus 112 and electrical stimulation apparatus 108 may be portable and may include different accessories, such as bands, to enable ultrasound apparatus 112 and electrical stimulation apparatus 108 to fit snugly or tightly onto the treated body region. It is noted that a portable ultrasound apparatus and stimulation apparatus 108 may use a gel that is encased between the treatment region 230 and the ultrasound apparatus 112.

The system of the disclosed technique may be adapted for personal use by an individual, such as at his/her home or at any convenient location, without necessitating a visit to a clinic or office in order to be treated by another person. The duration of a treatment session in accordance with the disclosed technique generally varies from about 15 to 45 minutes.

Reference is now made to FIG. 6, which illustrates system 600 for inducing persistent mechanical and electrical impedances of the body tissue for facilitating effective conveyance of low energy ultrasound energy to a treated internal tissue or organ, constructed and operative in accordance with one embodiment of the invention. System 600 is similar to system 100 of FIG. 2, and further includes the components of impedance monitoring apparatus 150 of FIG. 1. System 600 includes Ultrasound (US) apparatus or appliance 612 for applying low energy US onto an internal tissue/organ 640 (which is similar to internal organ/tissue 240). Appliance 612 includes non-invasive external US head 614. System 600 further includes electrical stimulation apparatus 608, and processor or controller 602 for controlling parameters of electrical stimulation apparatus 608 and of US appliance 612. The arrangement and operation of equivalent components of system 600, such as electrical stimulation apparatus 608, ultrasound appliance 612 and controller 602 is equivalent to the corresponding components of system 100 (e.g., ES apparatus 108, US apparatus 112, processor 102) and therefore not repeated, while particular aspects which are relevant to system 600 are described below. System 600 further includes impedance monitoring (tracking) apparatus 650 (equivalent to apparatus 150) which is connected to controller 602. Impedance monitoring apparatus 150 includes impedance transducers/sensors—which may simply comprise electrodes 608 and/or a designated electrode/sensor 654 which is disposed within US head 614 for interfacing the treated body, and/or thermal sensor 652, designated impedance transducers/sensors 651 and 656, remote transmitters/transducers/sensors 662 and monitor 654.

Impedance monitoring apparatus 650 may rely on the current readings which may be received in electrodes 611, and optionally also by transducer/sensor 654 in the form of an electrode 654 (disposed within the interface head 614 of ultrasound transducer 612), as well as further particular sensors 656 for enhancing reading capabilities and/or relieving electrodes 611, which are primarily employed for inducing electrical stimulation, from the reading task. The measuring of body electric impedance by electrodes 611, 654, and sensors 656 will usually be confined to the currents and frequencies utilized for the electric stimulation, which are not specifically selected for measuring body impedance. Accordingly, measurements may be carried out by designated currents at particular frequencies (or direct currents instead of an alternating current) which can be selected to better suit such measurements. To serve this goal, particular transducers/sensors 651 may be placed over treatment region 230, or in the vicinity thereof, as well as at other locations on the entire body part (e.g., the opposed side) in which treated internal organ 640 is disposed.

Designated impedance sensors/electrodes such as sensors (e.g., electrodes) 651 may be used in addition or in lieu or sensors 654, 656, wherein particular impedance measuring current is applied, i.e., a current at particular frequencies which are better suited for measuring the impedance. Sensors 651 may be dispersed over region 630, or its outskirts, but may also be placed outside region 630, displaced over the skin outside region 630, or disposed in a completely different location of the body, such as on the other side of the body part containing organ 640, wherein the treatment takes place. A further, alternative or additional, means for measuring impedance, is by mapping skin temperature, or temperature of treatment region 630, which is correlated to skin and body impedance, by thermal sensor 652 watching treatment region 630. The measured values of any of the sensors are intermittently or continuously fed to monitor 650 which calculates impedance values at treatment region 630. Transducers/Sensors 651, 656 are preferably non-invasive, and may also include a skin piercing element that enhances accuracy of readings. Further optionally, an externally disposed, thermal sensor 652 may be used for tracking skin temperature which is indicatively correlated to body impedance, for indirect tracking of changes in impedance.

Known available techniques such as those mentioned above [e.g., Bioelectrical Impedance Analysis (BIA), Bio-impedance Spectroscopy (BIS), and Electrical Impedance Myography (EIM)], may be applied by using transducers/sensors 651, 654 wherein the elected technology is applied by injecting electrical currents, either via some or all of transducers/sensors 651, 654 (which function either as sensors or as transmitters or both) and/or electrodes 611 (and/or sensors 656).

Ultrasound readings which are contemporarily used for diagnostic purposes, may also apply for directly measuring mechanical impedance in the context of the invention. Accordingly, impedance monitoring apparatus 650 may rely on US readings which are received at US head 614 (i.e., by transducer/sensor 654) or by particular transducers/sensors 651 (designed as US sensors, wherein the US transmitter is the head 614, but exchange of roles between sensing elements and transmitting elements can also be implemented with suitable equipment), and specifically by using the US diagnostics 658 described below.

In summary impedance monitoring apparatus 650 may include transducers/sensors for measuring impedance of a selected from a variety of options:

transducers/sensors for measuring electrical impedance (e.g., electrodes);
transducers/sensors for measuring mechanical impedance;
transducers/sensors for measuring body temperature;
transducers/sensors for measuring impedance between said electrodes;
transducers/sensors for measuring impedance between particular transducers/sensors;
transducers/sensors for measuring impedance between said electrodes and particular transducers/sensors;
transducers/sensors for measuring impedance by US diagnostics;
transducers/sensors for measuring impedance by an imaging apparatus; and
any combination of the above.

Any combination of the transducers/sensors discussed herein (e.g., transducers/sensors 611, 651, 656, 662 and 654—which can be configured as an electrode, or a particular transducer/sensor, or part of US diagnostics) may be installed and utilized, in parallel, simultaneously, or intermittently, and their independent findings may be compared, averaged, weighted, or manipulated for enhancing the overall accuracy of measurement, tracking and monitoring of body impedance.

Non-invasive external US appliance 612 is operational for applying low energy US energy, at an US frequency and an US intensity, onto a treatment region 630 over internal tissue/organ 640. Electrical stimulation (ES) apparatus 608 includes electrodes 611, arranged as two pairs 611A, and 611B of electrodes 611. ES apparatus 608 is operational for inducing interferential electrical stimulation, with electrodes 611 configured for positioning at crossed configuration onto the skin at treatment region 630 in proximity to internal tissue/organ 640. The interferential electrical stimulation is applied by ES apparatus 608, simultaneously with applying US energy by US appliance 612. Apparatus 1008 applies a first current at a first electric frequency and a first electric intensity via one of the two pairs of electrodes, i.e., pair 611A, and a second current at a second electric frequency and a second electric intensity via another of the pairs of electrodes, i.e., pair 611B. Thereby, an interference pattern of resonant waves that revolve at an interferential frequency in treatment region 630 is created by apparatus 608.

Controller 602 for controlling parameters of electrical stimulation apparatus 608 and US appliance 612, is operational, in addition to their control, for dynamically changing at least one of their parameters (ES parameters or US parameters, respectively), for maintaining the impedance of the body tissue in treatment region 630 within an impedance range. The parameters are selected from a group of electrical stimulation parameters and ultrasound parameters, including:

The interferential frequency. This frequency may be changed by dynamically changing the first electric frequency, or the second electric frequency, or both frequencies.

(ii) The interference pattern. This pattern may be changed by dynamically changing the first electric intensity, or the second electric intensity, or both intensities.
(iii) The US frequency.
(iv) The US intensity.

Impedance monitoring apparatus 650, which may be part of or integrated with electrical stimulation apparatus 608, represented by impedance monitor 652, is operational for continuously measuring and monitoring the electrical impedance in treatment region 630, e.g., between electrodes 611—particularly between the two electrodes of each pair 611A, 611B, or between any two electrodes 611, or between any electrode of electrodes 611 and a sensor 654 at US head 614 of appliance 612, or between further particular transducers/sensors 651, 654, 656. (when using other electromagnetic imaging technologies—remote thermal sensor 652, and/or remote transducers/sensor 662 may also be used). All of such sensors and/or electrodes which are deployed in or proximate to region 630, are connected to or linked with controller 602 and monitor 652, with adequate circuitry. Electrodes 611—when used as measuring electrodes in addition to providing ES stimulation, sensor 654 in head 614, sensors 651, 652, 662 and sensors 656 are connected (wired or by wireless communication) to monitor 650 and thus impedance is measured, preferably continuously, by adequate impedance measuring circuitry or software of monitor 650 or controller 602. Monitor 650 feeds, preferably continuously, the measured impedance values to controller 602. Controller 602 may than dynamically change the at least one parameter, in response to the electrical impedance as monitored by monitor 650, for maintaining the impedance within the predefined range.

To maintain the impedance within this range, controller 602 may dynamically change the at least one parameter by, at least one of the following:
 (a) when the electric impedance is monitored above the impedance range, at least one of:
  (1) reducing impedance by at least one of:
   (i) increasing at least one of: the first electric intensity and the second electric intensity
   (ii) reducing the interferential frequency by increasing frequency gap between the first electric frequency and the second electric frequency. This may be achieved by decreasing the lower frequency or by increasing the higher frequency, or by both actions.
  (2) increasing US penetration depth by at least one of:
   (i) decreasing the US frequency.
   (ii) increasing the US intensity.
 (b) when the electric impedance is monitored below the impedance range, at least one of:
  (1) increasing the impedance by at least one of:
   (i) reducing at least one of: the first electric intensity and the second electric intensity.
   (ii) increasing the interferential frequency by reducing frequency gap between the first electric frequency and the second electric frequency. This may be achieved by increasing the lower frequency or by decreasing the higher frequency, or by both actions.

(2) decreasing US penetration depth by at least one of:
(i) increasing the US frequency.
(ii) decreasing the US intensity.

Controller 602 may dynamically change another one of the parameters at a second pace, which is slower than the first pace at which the first parameter is changed, wherein the intensity and frequency of the ultrasound waves are maintained within the ultrasound range, such that at least one pattern of resonant ultrasound waves is effected to momentarily reach, through penetration depth 222, internal tissue/organ 640.

US energy is therefore applied to internal tissue/organ 640, while the impedance of the body tissue in treatment region 630 is maintained within the impedance range for effectuating or reinvigorating, any of the following:

Intensifying menstrual bleeding;
Regulating irregular menstruation;
Restoring menstruation;
Thickening endometrial lining;
Increase blood flow to/in the vicinity of the (female) organ;
Increase ovary dimension;
Increase ovarian follicle dimension;
Altering hormones regime (altering results from ovarian follicle treatment);
Clearing accretions, by the very force of US mechanical vibrations;
Increasing hormone concentration, as vibrated fat releases hormones; and
Treating ulcer, a closed wound, an internal injury, inflammation, and/or nerves.

US apparatus 600 may further include diagnostics/imaging apparatus 660 (similar to apparatus 160), such as US diagnostics 658 or imaging equipment represented by elements 662 (or radiating/sensing elements such as sensors of such equipment which may be disposed in US appliance head 614) for determining region 630 to be treated over internal tissue/organ 640, by identifying and mapping the location of internal tissue/organ 640. US diagnostics 658 may feature a separate, designated, equipment that is coupled with controller 602 for feeding its findings, or integrated with US head 614 or coupled therewith (e.g., transducer/sensor 654 may be an US element), for saving redundant equipment, as well as using the very same US head 614 for diagnostics and treatment, simultaneously or alternately. Imaging equipment 660 will usually include external elements, as well as elements integrated or coupled with US head 614, or electrodes 611, that eventually feed their readings to controller 602. Apparatus 600 includes display 603 or other interface means that help guide the user where to locate region 630 or determine its boundaries, where to place electrodes 611, and where to deploy head 614 for the effective treatment of internal tissue/organ 640. Diagnostics 658 may be used in addition to or instead of general diagnostic purposes, for measuring impedance, and in the case of mere US sensors—mechanical impedance of the body, and continuously feeding the reading to impedance monitoring apparatus 650 for triggering dynamic alterations of treatment parameters for maintaining impedance within a desired range.

Typically, interferential electrical stimulation apparatus 608 is configured to apply electrical stimulation at intensity in the electrical stimulation range of 1-70 mA. US appliance 612 is configured to transmits ultrasound waves at intensity in the ultrasound range of 0-2.1 Watt/cm$^2$, and the US frequency range of 0.7 MHz to 3.5 MHz.

Controller 602 may be configured to dynamically change the at least one parameter by altering the ultrasound transmission for example by any of the following:

change every 3-30 sec US change (intensity and/or frequency)
add or take US power by 0.1 W/cm$^2$ step at the time
increasing or decrease US frequency from 0.7 MHz to 3.5 MHz (back forth or back and forth)
change US intensity every 3-30 seconds, while maintaining US frequency constant for 3 minutes
change US frequency every 3-30 seconds, while maintaining US intensity constant for 3 minutes.

US apparatus 600 may further include massaging equipment, symbolically designated by icon 610, for massaging treatment region 630 simultaneously with the application of interferential electrical stimulation and the transmission of the ultrasound waves, for enhancing the effect of US action and for helping to prevent adaption of the body to electrical stimulation and the US energy, and thereby decreasing impedance change resulting from such adaptation.

The application of US apparatus 600 may further include the application of a gel 609 onto skin at treatment region 630 before transmitting the ultrasound waves.

Controller 602 may be configured to repeatedly dynamically change the at least one parameter, several times in one session. Typical session endurance may be around 40 minutes.

Controller 110 may dynamically change the at least one parameter by one or more of the following:

cyclic alternation of the waves of one pair of electrodes 611A or 611B, between the two opposed electrodes 611A, or 611B of the four electrodes 611.
gradually changing the phase shift between two constant—frequency (electric simulation) waves (wherein the phase of the wave in pair 611A is slightly shifted with respect to the phase of the wave in pair 611B), having similar or slightly shifted frequencies.

Figure 7:
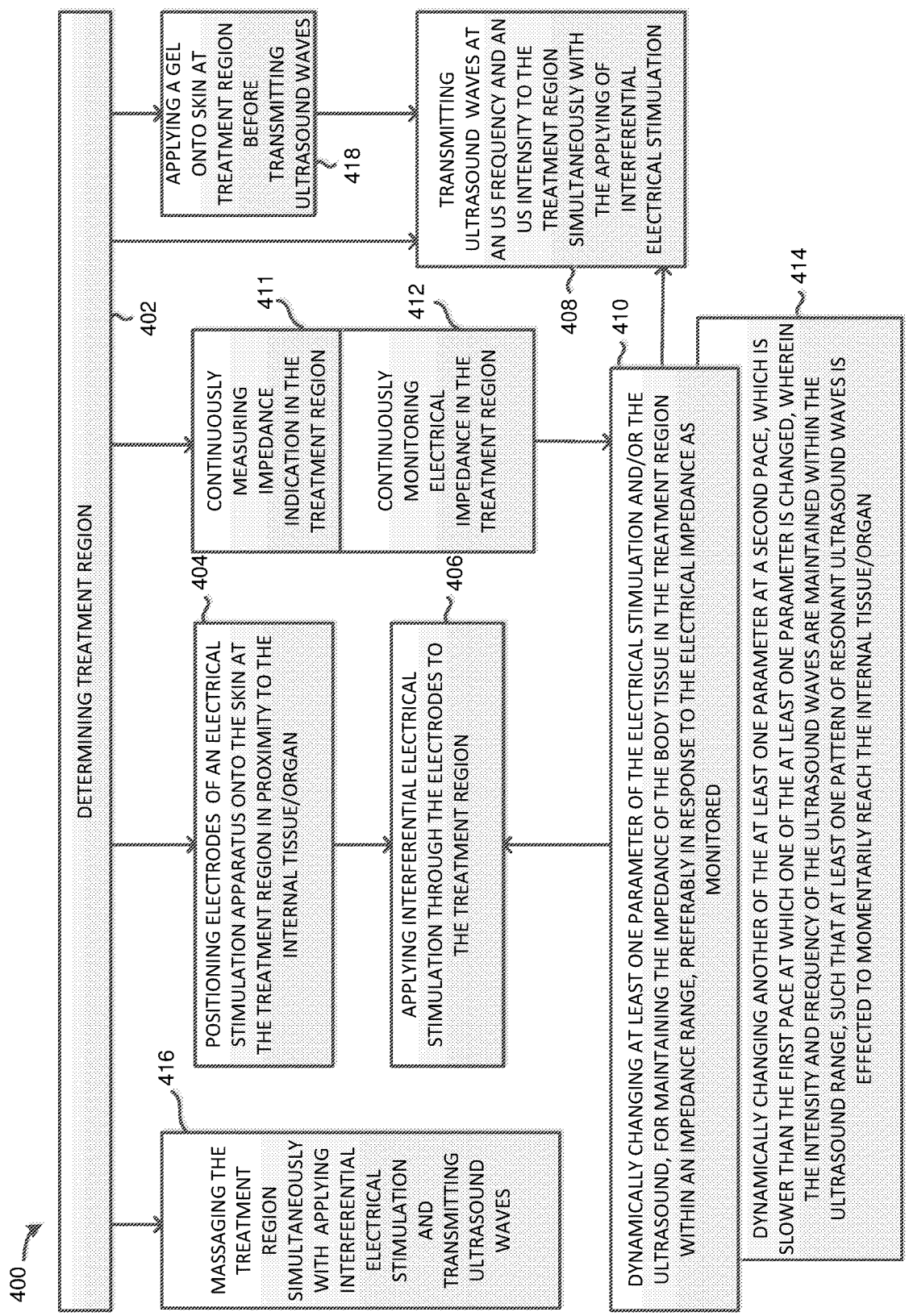
FIG. 7 is a block diagram of a method for inducing persistent mechanical and electrical impedances of the body tissue for facilitating effective conveyance of low energy ultrasound energy to the treated internal tissue or organ, operative in accordance with an embodiment of the invention.

Reference is now made to FIG. 7, which is a block diagram of method 400 for inducing persistent mechanical and electrical impedances of the body tissue for facilitating effective conveyance of low energy ultrasound energy to the treated internal tissue or organ, operative in accordance with an embodiment of the invention. Method 400 facilitates effective conveyance of low energy ultrasound (US) energy from a non-invasive external US source, to an internal body tissue/organ. Method 400 includes procedures 402-418. In procedure 402 a treatment region to be treated over the internal tissue/organ is determined. In Reference to FIG. 6, treatment region 630 is determined to be treated over internal tissue/organ 640.

In procedure 404 of method 400, electrodes of an electrical stimulation apparatus are positioned onto the skin at the treatment region in proximity to the internal organ. Two pairs of electrodes are placed at crossed configuration of an electrical stimulation apparatus which is operational for inducing interferential electrical stimulation. In Reference to FIG. 6, electrodes 611 of electrical stimulation apparatus 608 are positioned onto the skin at treatment region 630 in proximity to internal tissue/organ 640. Two pairs of electrodes, 611A, 611B, are placed at crossed configuration of electrical stimulation apparatus 608 which is operational for inducing interferential electrical stimulation.

In procedure 406, interferential electrical stimulation is applied through the electrodes to the treatment region, by applying a first current at a first electric frequency and a first electric intensity via one of the two pairs of electrodes, and a second current at a second electric frequency and a second electric intensity via another of the pairs of electrodes, thereby defining an interference pattern of resonant waves that revolve at an interferential frequency in the treatment region. In Reference to FIG. 6, interferential electrical stimulation is applied through electrodes 611 to treatment region 630, by applying a first current at a first electric frequency and a first electric intensity via one of the two pairs of electrodes—611A, and a second current at a second electric frequency and a second electric intensity via another of the pairs of electrodes—611B, thereby defining an interference pattern of resonant waves that revolve at an interferential frequency in treatment region 630.

In procedure 408 ultrasound (US) waves are transmitted at an US frequency and an US intensity to the treatment region simultaneously with the applying of interferential electrical stimulation. In Reference to FIG. 6, ultrasound (US) waves are transmitted at an US frequency and an US intensity to treatment region 630 simultaneously with the applying of interferential electrical stimulation.

In procedure 410, at least one parameter of the electrical stimulation and the ultrasound, is dynamically changed for maintaining the impedance of the body tissue in the treatment region within an impedance range. The parameter may be one of: (i) the interferential frequency, which can be changed by changing at least one of: the first electric frequency and the second electric frequency; (ii) the interference pattern, e.g., by changing at least one of: the first electric intensity and the second electric intensity; (iii) the US frequency; and (iv) the US intensity.

Method 400 further includes procedure 412 of continuously monitoring electrical impedance in the treatment region, e.g., between the electrodes, and/or the US head, and or deployed sensors. Procedure 412 is an example of the more generalized procedure 411 of continuously measuring impedance indication in the treatment region. According to procedure 411, impedance may be detected by one or more sensing and tracking means, including:

monitoring electrical impedance;
monitoring mechanical impedance;
monitoring body temperature;
monitoring impedance between electrodes of electrical stimulation;
monitoring impedance between particular transducers/sensors;
monitoring impedance between said electrodes and said particular transducers/sensors;
monitoring impedance by US diagnostics;
monitoring impedance by an imaging apparatus; and
monitoring impedance by any combination of the above.

With reference to FIG. 6, examples of such transducers/sensors include transducers/sensors 611, 651, 656, 662, and 654 (as an electrode, a particular transducer/sensor, or as an US diagnostics).

Procedure 410 of dynamically changing is activated (dynamically) in response to the electrical impedance as monitored in procedure 412 or the impedance as monitored in procedure 411, for maintaining the impedance within the predefined range. In Reference to FIG. 6, electrical impedance is continuously monitored in treatment region 630, e.g., between electrodes 611, and/or sensor 654 in US head 614, and or deployed sensors 656, and or transducers/sensors 651, 652 and 662. Such dynamically changing is activated (dynamically) in response to the electrical impedance as monitored by monitor 652, for maintaining the impedance within the predefined range.

Procedure 410 of dynamically changing may include:

(a) when the electric impedance is monitored above the impedance range, at least one of:
(1) reducing impedance by at least one of:
(i) increasing at least one of: the first electric intensity and the second electric intensity; and
(ii) reducing the interferential frequency by increasing frequency gap between the first electric frequency and the second electric frequency [by decreasing the lower frequency and/or increasing the higher frequency]; and
(2) increasing US penetration depth by at least one of:
(i) decreasing US frequency; and
(ii) increasing US intensity; and
(b) when the electric impedance is monitored below the impedance range, at least one of:
(1) increasing impedance by at least one of:
(i) reducing at least one of: the first electric intensity and the second electric intensity; and
(ii) increasing the interferential frequency by reducing frequency gap between the first electric frequency and the second electric frequency [by increasing the lower frequency and/or decreasing the higher frequency]; and
(2) decreasing US penetration depth by at least one of:
(i) increasing US frequency; and
(ii) decreasing US intensity.

Method 400 may further include procedure 414 of dynamically changing another of the at least one parameter at a second pace, which is slower than the first pace at which one of the at least one parameter is changed, wherein the intensity and frequency of the ultrasound waves are maintained within the ultrasound range, such that at least one pattern of resonant ultrasound waves is effected to momentarily reach internal tissue/organ 640 through depth penetration 222. In reference with FIG. 6, controller 602 dynamically changes another one of the parameters at a second pace, which is slower than the first pace at which the first parameter is changed, wherein the intensity and frequency of the ultrasound waves are maintained within the ultrasound range, such that at least one pattern of resonant ultrasound waves is effected to momentarily reach internal tissue/organ 640, through penetration depth 222.

The internal tissue/organ may include a female fertility organ, including the ovarian follicle, a blood vessel of the uterus (womb), the ovary, the endometrial lining, and/or the Fallopian tube, or any other tissue/organ, such as internal ulcer, a closed wound, internal injury, inflammation, or nerves. Method 400 may be directed at effectuating or reinvigorating at least one of:

intensifying menstrual bleeding;
regulating irregular menstruation;
restoring menstruation;
thickening endometrial lining;
increase blood flow to/in the vicinity of the (female) organ;
increase ovary dimension;
increase ovarian follicle dimension;
altering hormones regime [resulting from ovarian follicle treatment];
clearing accretions [by the force of mechanical vibrations];
increasing hormone concentration [vibrated fat releases hormones]
treating ulcer, closed wound, internal injury, inflammation, and/or nerves.

Procedure 404 of determining the region to be treated over the internal organ may include using US diagnostics or imaging for the determining. The diagnostics or imaging may be combined with ultrasound (US) treatment apparatus. In Reference to FIG. 6, US diagnostics 658 or imaging apparatus 660 is used for determining region 630 to be treated over internal tissue/organ 640. Diagnostics 658 or imaging apparatus 660 may be combined with ultrasound (US) appliance 612 or its head 614.

Procedure 406 of applying interferential electrical stimulation, may include applying electrical stimulation at intensity in the electrical stimulation range of 1-70 mA. Procedure 408 of transmitting ultrasound waves, may include transmitting ultrasound waves at intensity in the US range of 0-2.1 Watt/cm$^2$ and in the ultrasound frequency range of 0.7 MHz-3.5 MHz.

Procedure 410 of dynamically changing may include altering the ultrasound transmission by at least one selected from the list consisting of:
  change every 3-30 sec US change (intensity and/or frequency)
  add or take US power by 0.1 W/cm$^2$ step at the time
  increasing or decrease US frequency from 0.7 MHz to 3.5 MHz (back forth or back and forth)
  change US intensity every 3-30 seconds, while maintaining US frequency constant for 3 minutes
  change US frequency every 3-30 seconds, while maintaining US intensity constant for 3 minutes.

Method 400 may further include procedure 416 of massaging the treatment region simultaneously with procedures 406, 408 of applying interferential electrical stimulation and transmitting ultrasound waves.

Method 400 may further include procedure 418 of applying a gel, such as gel 609 of FIG. 6, onto skin at treatment region 630 before the procedure of transmitting ultrasound waves;

Procedure 410 may include repeating the change several times in one session. A session may endure around 40 mins. Procedure 410 of dynamically changing may include at least one selected from the list consisting of:
  cyclic alternation of the waves of a pair of electrodes between two opposed pairs of 4 electrodes; and
  gradually changing the phase shift between two constant—frequency-waves having similar or slightly shifted frequencies, as described with reference to FIG. 6.

It will be appreciated by persons skilled in the art that the technique is not limited to what has been particularly shown and described hereinabove.

The invention claimed is:

1. Ultrasound (US) apparatus for applying low energy US onto an internal tissue/organ, comprising:
  (a) a non-invasive external US appliance configured to apply low energy US energy, at an US frequency and an US intensity, onto a treatment region over the internal tissue/organ;
  (b) an electrical stimulation apparatus comprising two pairs of electrodes configured to induce interferential electrical stimulation configured for positioning at crossed configuration onto the skin at the treatment region in proximity to the internal tissue/organ, by applying, simultaneously with said applying US energy, a first current at a first electric frequency and a first electric intensity via one of said two pairs of electrodes, and a second current at a second electric frequency and a second electric intensity via another of said pairs of electrodes, thereby defining an interference pattern of resonant waves that revolve at an interferential frequency in said treatment region;
  (c) an impedance monitoring apparatus configured to continuously track and monitor the impedance of a body tissue in said treatment region;
  (d) a controller for controlling parameters of said electrical stimulation apparatus and said US appliance, configured to dynamically change at least one of said parameters in response to the impedance monitored by said monitoring apparatus, for maintaining said impedance within a predefined impedance range, wherein said parameters are selected from the group of electrical stimulation parameters and ultrasound parameters consisting of: (i) said interferential frequency; (ii) said interference pattern; (iii) said US frequency; and (iv) said US intensity.

2. The US apparatus of claim 1, wherein said impedance monitoring apparatus comprises transducers/sensors for measuring impedance selected from the list consisting of:
  transducers/sensors for measuring electrical impedance;
  transducers/sensors for measuring mechanical impedance;
  transducers/sensors for measuring body temperature;
  transducers/sensors for measuring impedance between electrical stimulation electrodes;
  transducers/sensors for measuring impedance between particular transducers/sensors;
  transducers/sensors for measuring impedance between said electrodes and particular transducers/sensors;
  transducers/sensors for measuring impedance by US diagnostics;
  transducers/sensors for measuring impedance by an imaging apparatus; and
  any combination of the above.

3. The US apparatus of claim 1, wherein said controller dynamically changes said at least one of said parameters by:
  (a) when said impedance is monitored above said impedance range, at least one of:
    (1) reducing impedance by at least one of:
      (i) increasing at least one of: said first electric intensity and said second electric intensity; and
      (ii) reducing said interferential frequency by increasing frequency gap between said first electric frequency and said second electric frequency; and
    (2) increasing US penetration depth by at least one of:
      (i) decreasing said US frequency; and
      (ii) increasing said the US intensity; and
  (b) when said impedance is monitored below said impedance range, at least one of:
    (1) increasing the impedance by at least one of:
      (i) reducing at least one of: said first electric intensity and said second electric intensity; and
      (ii) increasing said interferential frequency by reducing frequency gap between said first electric frequency and said second electric frequency; and
    (2) decreasing US penetration depth by at least one of:
      (i) increasing said US frequency; and
      (ii) decreasing said US intensity.

4. The US apparatus of claim 1, wherein said controller dynamically changes another of said at least one of said parameters at a second pace, which is slower than a first pace by which said at least one of said parameters is changed, wherein the intensity and frequency of a ultrasound waves are maintained within said ultrasound range, such that at least one pattern of resonant ultrasound waves is effected to momentarily reach said internal tissue/organ.

5. The US apparatus of claim 1, wherein said controller dynamically changes said at least one of said parameters by at least one selected from the list consisting of:

altering said ultrasound transmission by 3-30 sec per US change;

altering said ultrasound transmission by adding/taking US power by 0.1 W/cm$^2$;

altering said ultrasound transmission by increasing/decreasing US frequency from 0.7 MHz to 3.5 MHz;

altering said ultrasound transmission by every 3-30 seconds, when changing US power, maintaining US frequency constant 3-30 for 3 minutes;

altering said ultrasound transmission by every 3-30 seconds, when changing US frequency, maintaining US power constant for 3 minutes;

cyclic alternation of a waves of a pair of electrodes between two opposed pairs of 4 electrodes; and gradually changing a phase shift between two constant-frequency-waves having similar or slightly shifted frequencies;

changing said at least one of said parameters several times in one session;

changing said interferential frequency by changing at least one of:
  i. said first electric frequency; and
  ii. said second electric frequency;

changing said interference pattern by changing at least one of:
  i. said first electric intensity; and
  ii. said second electric intensity;

increasing said interferential frequency by reducing frequency gap between said first electric frequency and said second electric frequency, by at least one of:
  i. increasing a lower frequency; and
  ii. decreasing a higher frequency decreasing said interferential frequency by increasing frequency gap between said first electric frequency and said second electric frequency, by at least one of:
  i. decreasing the lower frequency; and
  ii. increasing the higher frequency.

6. The US apparatus of claim 1, further comprising US diagnostics and/or imaging equipment for determining the region to be treated over said internal tissue/organ.

7. The US apparatus of claim 1, further comprising at least one of: (a) said interferential electrical stimulation apparatus which is configured to apply electrical stimulation at intensity in the electrical stimulation range of 1-70 mA; and (b) said US appliance which is configured to transmit ultrasound waves at intensity in the ultrasound range of 0.7 MHz-3.5 MHz, 0-2.1 Watt/cm$^2$.

8. The US apparatus of claim 1, wherein said internal tissue/organ includes a female fertility organ, ulcer, closed wound, internal injury, inflammation, or nerves.

9. The US apparatus of claim 8, wherein said female fertility organ comprises at least one of:
  ovarian follicle;
  blood vessel of the uterus (womb);
  ovary;
  endometrial lining; and
  Fallopian tube.

10. The US apparatus of claim 8, wherein said US energy is applied, while maintaining the impedance of the body tissue in said treatment region within said impedance range for effectuating/reinvigorating, at least one of:
  intensifying menstrual bleeding;
  regulating irregular menstruation;
  restoring menstruation;
  thickening endometrial lining;
  increase blood flow to/in the vicinity of said (female) organ;
  increase ovary dimension;
  increase ovarian follicle dimension;
  altering hormones regime;
  clearing accretions;
  increasing hormone concentration; and
  treating ulcer, closed wound, internal injury, inflammation, and/or nerves.

11. Method for applying low energy ultrasound (US) energy from a non-invasive external US source to an internal body tissue/organ, the method comprising the procedures of:
  (a) determining a treatment region over the internal tissue/organ;
  (b) positioning onto the skin at the treatment region in proximity to the internal tissue/organ, two pairs of electrodes at crossed configuration of an electrical stimulation apparatus operational for inducing interferential electrical stimulation;
  (c) applying interferential electrical stimulation through the electrodes to the treatment region, by applying a first current at a first electric frequency and a first electric intensity via one of said two pairs of electrodes, and a second current at a second electric frequency and a second electric intensity via another of said pairs of electrodes, thereby defining an interference pattern of resonant waves that revolve at an interferential frequency in said treatment region;
  (d) transmitting ultrasound (US) waves at an US frequency and an US intensity to the treatment region simultaneously with said applying of interferential electrical stimulation;
  (e) continuously monitoring impedance tracked in the treatment region; and
  (f) dynamically changing at least one parameter of said electrical stimulation and said ultrasound, in response to the impedance as monitored, for maintaining the impedance of the body tissue in said treatment region within a predefined impedance range, wherein said parameter comprising one of: (i) said interferential frequency; (ii) said interference pattern; (iii) said US frequency; and (iv) said US intensity.

12. The method of claim 11, wherein said procedure (e) of continuously monitoring impedance further comprises at least one selected from the list consisting of:
  monitoring electrical impedance between electrical stimulation electrodes;
  monitoring mechanical impedance;
  monitoring body temperature;
  monitoring impedance between said electrodes;
  monitoring impedance between particular transducers/sensors;
  monitoring impedance between said electrodes and particular transducers/sensors;
  monitoring impedance by US diagnostics;
  monitoring impedance by an imaging apparatus; and
  monitoring impedance by any combination of the above.

13. The method of claim 11, wherein said procedure of (f) dynamically changing comprises:
  (a) when said impedance is monitored above said impedance range, at least one of:
    (1) reducing impedance by at least one of:
      (i) increasing at least one of: said first electric intensity and said second electric intensity; and
      (ii) reducing said interferential frequency by increasing frequency gap between said first electric frequency and said second electric frequency; and
    (2) increasing US penetration depth by at least one of:
      (i) decreasing US frequency; and (ii) increasing US intensity; and
(b) when said electric impedance is monitored below said impedance range, at least one of:
(1) increasing impedance by at least one of:
(i) reducing at least one of: said first electric intensity and said second electric intensity; and
(ii) increasing said interferential frequency by reducing frequency gap between said first electric frequency and said second electric frequency; and
(2) decreasing US penetration depth by at least one of:
(i) increasing US frequency; and
(ii) decreasing US intensity.

14. The method of claim 11, further comprising the procedure of:
(g) dynamically changing another of said at least one parameter at a second pace, which is slower than a first pace by which at least one of said parameter is changed, wherein the intensity and frequency of a ultrasound waves are maintained within said ultrasound range, such that at least one pattern of resonant ultrasound waves is effected to momentarily reach said internal tissue/organ.

15. The method of claim 11, wherein said procedure of (f) dynamically changing comprises at least one selected from the list consisting of:
altering said ultrasound transmission by 3-30 seconds per change;
altering said ultrasound transmission by adding/taking power by 0.1 W/cm$^2$;
altering said ultrasound transmission by increasing/decreasing frequency from 0.7 MHz to 3.5 MHz;
altering said ultrasound transmission by every 3-30 seconds, when changing power/frequency keeping frequency/power constant for 3 min. and vice versa;
cyclic alternation of a waves of a pair of electrodes between two opposed pairs of 4 electrodes; and
gradually changing a phase shift between two constant-frequency-waves having similar or slightly shifted frequencies;
changing said at least one parameter several times in one session;
changing said interferential frequency by changing at least one of:
i. said first electric frequency; and
ii. said second electric frequency;
changing said interference pattern by changing at least one of:
i. said first electric intensity; and
ii. said second electric intensity;
increasing said interferential frequency by reducing frequency gap between said first electric frequency and said second electric frequency, by at least one of:
i. increasing a lower frequency; and
ii. decreasing a higher frequency; and
decreasing said interferential frequency by increasing frequency gap between said first electric frequency and said second electric frequency, by at least one of:
i. decreasing the lower frequency; and
ii. increasing the higher frequency.

16. The method of claim 11, wherein said procedure of (a) determining the region to be treated over the internal tissue/organ comprises using US diagnostics and/or imaging for said determining.

17. The method of claim 11, further comprising at least one of: (i) said procedure of (c) applying interferential electrical stimulation, comprises applying electrical stimulation at intensity in the electrical stimulation range of 1-70 mA; and (ii) said procedure of (d) transmitting ultrasound waves, comprises transmitting ultrasound waves at intensity in the ultrasound range of 0.7 MHz-3.5 MHz, 0-2.1 Watt/cm$^2$.

18. The method of claim 11, wherein said internal tissue/organ includes a female fertility organ, ulcer, internal injury, closed wound, inflammation, or nerves.

19. The method of claim 18, wherein said female fertility organ comprises at least one of:
ovarian follicle;
blood vessel of the uterus (womb);
ovary;
endometrial lining; and
Fallopian tube.

20. The method of claim 18, wherein said method is directed at effectuating/reinvigorating at least one of:
intensifying menstrual bleeding;
regulating irregular menstruation;
restoring menstruation;
thickening endometrial lining;
increase blood flow to/in the vicinity of said tissue/organ;
increase ovary dimension;
increase ovarian follicle dimension;
altering hormones regime;
clearing accretions;
increasing hormone concentration; and
treating ulcer, closed wound, internal injury, inflammation, and/or nerves.

* * * * *